(12) United States Patent
Wellig et al.

(10) Patent No.: US 11,778,423 B2
(45) Date of Patent: Oct. 3, 2023

(54) USING SMART OCCUPANCY DETECTION AND CONTROL IN BUILDINGS TO REDUCE DISEASE TRANSMISSION

(71) Applicant: Honeywell International Inc., Charlotte, NC (US)

(72) Inventors: Armin Wellig, Mont-sur-Rolle (CH); Chris Inkpen, Charlotte, NC (US); Kelvin Towler, Barnham (GB)

(73) Assignee: HONEYWELL INTERNATIONAL INC., Charlotte, NC (US)

( * ) Notice: Subject to any disclaimer, the term of this patent is extended or adjusted under 35 U.S.C. 154(b) by 0 days.

(21) Appl. No.: 17/518,128

(22) Filed: Nov. 3, 2021

(65) Prior Publication Data

US 2022/0060856 A1    Feb. 24, 2022

Related U.S. Application Data

(63) Continuation of application No. 16/907,044, filed on Jun. 19, 2020, now Pat. No. 11,184,739.

(51) Int. Cl.
  *H04W 4/029*  (2018.01)
  *G16H 50/80*  (2018.01)
  (Continued)

(52) U.S. Cl.
  CPC ............ *H04W 4/029* (2018.02); *G16H 50/80* (2018.01); *H04W 4/021* (2013.01); *H04W 4/33* (2018.02)

(58) Field of Classification Search
  CPC ....... H04W 4/029; H04W 4/021; H04W 4/33; G16H 50/80; G16H 15/00; G16H 40/20;
  (Continued)

(56) References Cited

U.S. PATENT DOCUMENTS

| 191,512 A | 6/1877 | Bennett et al. |
|---|---|---|
| 4,009,647 A | 3/1977 | Howorth |

(Continued)

FOREIGN PATENT DOCUMENTS

| CA | 2387100 A1 | 11/2003 |
|---|---|---|
| CA | 2538139 A1 | 3/2005 |

(Continued)

OTHER PUBLICATIONS

Olken et al., "Object Lessons Learned from a Distributed System for Remote Building Monitoring and Operation," ACM SIGPLAN Notices, vol. 33, No. 10, pp. 284-295, Oct. 1998.

(Continued)

*Primary Examiner* — Eric Blount
(74) *Attorney, Agent, or Firm* — Seager, Tufte & Wickhem, LLP

(57) ABSTRACT

A signal is received from an occupancy sensor each time a person passes through an access point corresponding to a building space, and is identified as indicating a person either entering or exiting the building space. An occupancy count is maintained for each of the building spaces by incrementing the occupancy count when the signal indicates a person entering and decrementing the occupancy count when the signal indicates a person exiting. A determination is made as to whether the occupancy count for any of the building spaces of the plurality of building spaces has reached a threshold for the corresponding building space. Action is taken in response to determining that the occupancy count for any of the building spaces of the plurality of building spaces has reached the threshold for that particular building space.

20 Claims, 8 Drawing Sheets

(51) Int. Cl.
*H04W 4/33* (2018.01)
*H04W 4/021* (2018.01)

(58) Field of Classification Search
CPC ........ G16H 40/63; G16H 50/70; G08B 21/02; G08B 21/0476; G08B 21/245; G08B 21/22; A61L 2/10; A61L 2202/14; A61L 2202/25; A61L 2209/111
USPC ...................................................... 340/573.1
See application file for complete search history.

(56) References Cited

U.S. PATENT DOCUMENTS

| | | | |
|---|---|---|---|
| 4,375,637 A | 3/1983 | Desjardins | |
| 4,918,615 A | 4/1990 | Suzuki et al. | |
| 4,939,922 A | 7/1990 | Smalley et al. | |
| 5,566,084 A | 10/1996 | Cmar | |
| 5,727,579 A | 3/1998 | Chardack | |
| 5,745,126 A | 4/1998 | Jain et al. | |
| 5,751,916 A | 5/1998 | Kon et al. | |
| 5,777,598 A | 7/1998 | Gowda et al. | |
| 5,973,662 A | 10/1999 | Singers et al. | |
| 6,065,842 A | 5/2000 | Fink | |
| 6,139,177 A | 10/2000 | Venkatraman et al. | |
| 6,144,993 A | 11/2000 | Fukunaga et al. | |
| 6,157,943 A | 12/2000 | Meyer | |
| 6,229,429 B1 | 5/2001 | Horan | |
| 6,238,337 B1 | 5/2001 | Kambhatla et al. | |
| 6,334,211 B1 | 12/2001 | Kojima et al. | |
| 6,353,853 B1 | 3/2002 | Gravlin | |
| 6,369,695 B2 | 4/2002 | Horan | |
| 6,375,038 B1 | 4/2002 | Daansen et al. | |
| 6,429,868 B1 | 8/2002 | Dehner, Jr. et al. | |
| 6,473,084 B1 | 10/2002 | Phillips et al. | |
| 6,487,457 B1 | 11/2002 | Hull et al. | |
| 6,580,950 B1 | 6/2003 | Johnson et al. | |
| 6,598,056 B1 | 7/2003 | Hull et al. | |
| 6,619,555 B2 | 9/2003 | Rosen | |
| 6,704,012 B1 | 3/2004 | Lefave | |
| 6,712,269 B1 | 3/2004 | Watkins | |
| 6,720,874 B2 | 4/2004 | Fufido et al. | |
| 6,741,915 B2 | 5/2004 | Poth | |
| 6,796,896 B2 | 9/2004 | Laiti | |
| 6,801,199 B1 | 10/2004 | Wallman | |
| 6,816,878 B1 | 11/2004 | Zimmers et al. | |
| 6,876,951 B2 | 4/2005 | Skidmore et al. | |
| 6,882,278 B2 | 4/2005 | Winings et al. | |
| 6,904,385 B1 | 6/2005 | Budike, Jr. | |
| 6,907,387 B1 | 6/2005 | Reardon | |
| 6,911,177 B2 | 6/2005 | Deal | |
| 6,993,403 B1 | 1/2006 | Dadebo et al. | |
| 6,993,417 B2 | 1/2006 | Osann, Jr. | |
| 7,023,440 B1 | 4/2006 | Havekost et al. | |
| 7,031,880 B1 | 4/2006 | Seem et al. | |
| 7,062,722 B1 | 6/2006 | Carlin et al. | |
| 7,110,843 B2 | 9/2006 | Pagnano et al. | |
| 7,139,685 B2 | 11/2006 | Bascle et al. | |
| 7,164,972 B2 | 1/2007 | Imhof et al. | |
| 7,183,899 B2 | 2/2007 | Behnke | |
| 7,200,639 B1 | 4/2007 | Yoshida | |
| 7,222,111 B1 | 5/2007 | Budike, Jr. | |
| 7,222,800 B2 | 5/2007 | Wruck | |
| 7,257,397 B2 | 8/2007 | Shamoon et al. | |
| 7,280,030 B1 | 10/2007 | Monaco | |
| 7,292,908 B2 | 11/2007 | Borne et al. | |
| 7,295,116 B2 | 11/2007 | Kumar et al. | |
| 7,302,313 B2 | 11/2007 | Sharp et al. | |
| 7,308,323 B2 | 12/2007 | Kruk et al. | |
| 7,308,388 B2 | 12/2007 | Beverina et al. | |
| 7,313,447 B2 | 12/2007 | Hsiung et al. | |
| 7,346,433 B2 | 3/2008 | Budike, Jr. | |
| 7,356,548 B1 | 4/2008 | Culp et al. | |
| 7,379,782 B1 | 5/2008 | Cocco | |
| 7,383,148 B2 | 6/2008 | Ahmed | |
| 7,434,742 B2 | 10/2008 | Mueller et al. | |
| 7,447,333 B1 | 11/2008 | Masticola et al. | |
| 7,466,224 B2 | 12/2008 | Ward et al. | |
| 7,496,472 B2 | 2/2009 | Seem | |
| 7,512,450 B2 | 3/2009 | Ahmed | |
| 7,516,490 B2 | 4/2009 | Riordan et al. | |
| 7,548,833 B2 | 6/2009 | Ahmed | |
| 7,551,092 B1 | 6/2009 | Henry | |
| 7,557,729 B2 | 7/2009 | Hubbard et al. | |
| 7,567,844 B2 | 7/2009 | Thomas et al. | |
| 7,596,473 B2 | 9/2009 | Hansen et al. | |
| 7,610,910 B2 | 11/2009 | Ahmed | |
| 7,626,507 B2 | 12/2009 | LaCasse | |
| 7,664,574 B2 | 2/2010 | Imhof et al. | |
| 7,682,464 B2 | 3/2010 | Glenn et al. | |
| 7,688,212 B2 * | 3/2010 | Farley ...................... | G08B 7/06 340/8.1 |
| 7,702,421 B2 | 4/2010 | Sullivan et al. | |
| 7,729,882 B2 | 6/2010 | Seem | |
| 7,755,494 B2 | 7/2010 | Melker et al. | |
| 7,761,310 B2 | 7/2010 | Rodgers | |
| 7,774,227 B2 | 8/2010 | Srivastava | |
| 7,797,188 B2 | 9/2010 | Srivastava | |
| 7,819,136 B1 | 10/2010 | Eddy | |
| 7,822,806 B2 | 10/2010 | Frank et al. | |
| 7,856,370 B2 | 12/2010 | Katta et al. | |
| 7,944,358 B2 | 5/2011 | Sorensen et al. | |
| 7,978,083 B2 | 7/2011 | Melker et al. | |
| 7,984,384 B2 | 7/2011 | Chaudhri et al. | |
| 7,986,323 B2 | 7/2011 | Kobayashi et al. | |
| 8,024,666 B2 | 9/2011 | Thompson | |
| 8,086,047 B2 | 12/2011 | Penke et al. | |
| 8,099,178 B2 | 1/2012 | Mairs et al. | |
| 8,151,280 B2 | 4/2012 | Sather et al. | |
| 8,176,095 B2 | 5/2012 | Murray et al. | |
| 8,218,871 B2 | 7/2012 | Angell et al. | |
| 8,219,660 B2 | 7/2012 | McCoy et al. | |
| 8,271,941 B2 | 9/2012 | Zhang et al. | |
| 8,294,585 B2 | 10/2012 | Barnhill | |
| 8,302,020 B2 | 10/2012 | Louch et al. | |
| 8,320,634 B2 | 11/2012 | Deutsch | |
| 8,334,422 B2 | 12/2012 | Gutsol et al. | |
| 8,344,893 B1 | 1/2013 | Drammeh | |
| 8,375,118 B2 | 2/2013 | Hao et al. | |
| 8,476,590 B2 | 7/2013 | Stratmann et al. | |
| 8,516,016 B2 | 8/2013 | Park et al. | |
| 8,558,660 B2 | 10/2013 | Nix et al. | |
| 8,639,527 B2 | 1/2014 | Rensvold et al. | |
| 8,698,637 B2 | 4/2014 | Raichman | |
| 8,816,860 B2 | 8/2014 | Ophardt et al. | |
| 8,869,027 B2 | 10/2014 | Louch et al. | |
| 8,904,497 B2 | 12/2014 | Hsieh | |
| 8,936,944 B2 | 1/2015 | Peltz et al. | |
| 8,947,437 B2 | 2/2015 | Garr et al. | |
| 8,950,019 B2 | 2/2015 | Loberger et al. | |
| 9,000,926 B2 | 4/2015 | Hollock et al. | |
| 9,030,325 B2 | 5/2015 | Faneff | |
| 9,098,738 B2 | 8/2015 | Bilet et al. | |
| 9,105,071 B2 | 8/2015 | Fletcher et al. | |
| 9,175,356 B2 | 11/2015 | Peltz et al. | |
| 9,240,111 B2 | 1/2016 | Scott et al. | |
| 9,280,884 B1 | 3/2016 | Schultz et al. | |
| 9,292,972 B2 | 3/2016 | Hailemariam et al. | |
| 9,320,662 B2 | 4/2016 | Hayes et al. | |
| 9,370,600 B1 | 6/2016 | DuPuis et al. | |
| 9,373,242 B1 | 6/2016 | Conrad et al. | |
| 9,396,638 B2 | 7/2016 | Wildman et al. | |
| 9,311,807 B2 | 8/2016 | Schultz et al. | |
| 9,406,212 B2 | 8/2016 | De Luca et al. | |
| 9,418,535 B1 | 8/2016 | Felch et al. | |
| 9,418,536 B1 | 8/2016 | Felch et al. | |
| 9,449,219 B2 | 9/2016 | Bilet et al. | |
| 9,477,543 B2 | 10/2016 | Henley et al. | |
| 9,497,832 B2 | 11/2016 | Verberkt et al. | |
| 9,513,364 B2 | 12/2016 | Hall et al. | |
| 9,526,380 B2 | 12/2016 | Hamilton et al. | |
| 9,526,806 B2 | 12/2016 | Park et al. | |
| 9,536,415 B2 | 1/2017 | De Luca et al. | |
| 9,558,648 B2 | 1/2017 | Douglas | |
| 9,591,267 B2 | 3/2017 | Lipton et al. | |

(56) References Cited

U.S. PATENT DOCUMENTS

| | | | |
|---|---|---|---|
| 9,613,518 B2 | 4/2017 | Dunn et al. |
| 9,618,224 B2 | 4/2017 | Emmons et al. |
| 9,618,918 B2 | 4/2017 | O'Keeffe |
| 9,640,059 B2 | 5/2017 | Hyland |
| 9,672,360 B2 | 6/2017 | Barkan |
| 9,710,700 B2 | 7/2017 | Bilet et al. |
| 9,715,242 B2 | 7/2017 | Pillai et al. |
| 9,721,452 B2 | 8/2017 | Felch et al. |
| 9,729,945 B2 | 8/2017 | Schultz et al. |
| 9,784,464 B2 | 10/2017 | Yamamoto et al. |
| 9,843,743 B2 | 12/2017 | Lewis et al. |
| 9,856,634 B2 | 1/2018 | Rodenbeck et al. |
| 9,872,088 B2 | 1/2018 | Fadell et al. |
| 9,875,639 B2 | 1/2018 | Bone et al. |
| 9,911,312 B2 | 3/2018 | Wildman et al. |
| 9,940,819 B2 | 4/2018 | Ferniany |
| 9,956,306 B2 | 5/2018 | Brais et al. |
| 9,986,175 B2 | 5/2018 | Frank et al. |
| 10,087,608 B2 | 10/2018 | Dobizl |
| 10,223,894 B2 | 3/2019 | Raichman |
| 10,228,837 B2 | 3/2019 | Hua et al. |
| 10,235,865 B2 | 3/2019 | Thyroff |
| 10,251,610 B2 | 4/2019 | Parthasarathy et al. |
| 10,298,411 B2 | 5/2019 | Donlan et al. |
| 10,303,843 B2 | 5/2019 | Bitran et al. |
| 10,332,382 B2 | 6/2019 | Thyroff |
| 10,382,893 B1 | 8/2019 | Wootton et al. |
| 10,469,590 B2 | 11/2019 | Scanlin et al. |
| 10,514,817 B2 | 12/2019 | Hua et al. |
| 10,565,844 B2 | 2/2020 | Pourmohammad et al. |
| 10,602,474 B2 | 3/2020 | Goldstein |
| 10,607,147 B2 * | 3/2020 | Raykov ................ G06N 20/00 |
| 10,613,504 B2 | 4/2020 | Chowdhury |
| 10,691,081 B2 | 6/2020 | Ray et al. |
| 10,708,154 B2 | 7/2020 | Pefkianakis et al. |
| 10,866,003 B2 * | 12/2020 | Ajax ....................... F24F 11/56 |
| 10,944,830 B2 * | 3/2021 | Scanlin ................... F24F 11/63 |
| 11,184,739 B1 * | 11/2021 | Wellig ................... G16H 50/70 |
| 2002/0111698 A1 | 8/2002 | Graziano et al. |
| 2002/0130868 A1 | 9/2002 | Smith |
| 2003/0028269 A1 | 2/2003 | Spriggs et al. |
| 2003/0030637 A1 | 2/2003 | Grinstein et al. |
| 2003/0046862 A1 | 3/2003 | Wolf et al. |
| 2003/0071814 A1 | 4/2003 | Jou et al. |
| 2003/0078677 A1 | 4/2003 | Hull et al. |
| 2003/0083957 A1 | 5/2003 | Olefson |
| 2003/0103075 A1 | 6/2003 | Rosselot |
| 2003/0171851 A1 | 9/2003 | Brickfield et al. |
| 2003/0214400 A1 | 11/2003 | Mizutani et al. |
| 2003/0233432 A1 | 12/2003 | Davis et al. |
| 2004/0001009 A1 | 1/2004 | Winings et al. |
| 2004/0064260 A1 | 4/2004 | Padmanabhan et al. |
| 2004/0143474 A1 | 7/2004 | Haeberle et al. |
| 2004/0153437 A1 | 8/2004 | Buchan |
| 2004/0168115 A1 | 8/2004 | Bauernschmidt et al. |
| 2004/0233192 A1 | 11/2004 | Hopper |
| 2004/0260411 A1 | 12/2004 | Cannon |
| 2005/0010460 A1 | 1/2005 | Mizoguchi et al. |
| 2005/0119767 A1 | 6/2005 | Kiwimagi et al. |
| 2005/0143863 A1 | 6/2005 | Ruane et al. |
| 2005/0267900 A1 | 12/2005 | Ahmed et al. |
| 2006/0004841 A1 | 1/2006 | Heikkonen et al. |
| 2006/0009862 A1 | 1/2006 | Imhof et al. |
| 2006/0017547 A1 | 1/2006 | Buckingham et al. |
| 2006/0020177 A1 | 1/2006 | Seo et al. |
| 2006/0028471 A1 | 2/2006 | Kincaid et al. |
| 2006/0029256 A1 | 2/2006 | Miyoshi et al. |
| 2006/0058900 A1 | 3/2006 | Johanson et al. |
| 2006/0067545 A1 | 3/2006 | Lewis et al. |
| 2006/0067546 A1 | 3/2006 | Lewis et al. |
| 2006/0077255 A1 | 4/2006 | Cheng |
| 2006/0184326 A1 | 8/2006 | McNally et al. |
| 2006/0231568 A1 | 10/2006 | Lynn et al. |
| 2006/0265664 A1 | 11/2006 | Simons et al. |
| 2006/0279630 A1 | 12/2006 | Aggarwal et al. |
| 2007/0016955 A1 | 1/2007 | Goldberg et al. |
| 2007/0055757 A1 | 3/2007 | Mairs et al. |
| 2007/0055760 A1 | 3/2007 | McCoy et al. |
| 2007/0061046 A1 | 3/2007 | Mairs et al. |
| 2007/0067062 A1 | 3/2007 | Mairs et al. |
| 2007/0088534 A1 | 4/2007 | MacArthur et al. |
| 2007/0090951 A1 | 4/2007 | Chan et al. |
| 2007/0091091 A1 | 4/2007 | Gardiner et al. |
| 2007/0101433 A1 | 5/2007 | Louch et al. |
| 2007/0114295 A1 | 5/2007 | Jenkins |
| 2007/0120652 A1 | 5/2007 | Behnke |
| 2007/0139208 A1 | 6/2007 | Kates |
| 2007/0216682 A1 | 9/2007 | Navratil et al. |
| 2007/0219645 A1 | 9/2007 | Thomas et al. |
| 2007/0239484 A1 | 10/2007 | Arond et al. |
| 2007/0268122 A1 | 11/2007 | Kow et al. |
| 2007/0285510 A1 | 12/2007 | Lipton et al. |
| 2008/0001763 A1 | 1/2008 | Raja et al. |
| 2008/0027885 A1 | 1/2008 | Van Putten et al. |
| 2008/0036593 A1 | 2/2008 | Rose-Pehrsson et al. |
| 2008/0062167 A1 | 3/2008 | Boggs et al. |
| 2008/0067244 A1 | 3/2008 | Marks |
| 2008/0099045 A1 | 5/2008 | Glenn et al. |
| 2008/0103798 A1 | 5/2008 | Domenikos et al. |
| 2008/0120396 A1 | 5/2008 | Jayaram et al. |
| 2008/0144885 A1 | 6/2008 | Zucherman et al. |
| 2008/0183424 A1 | 7/2008 | Seem |
| 2008/0194009 A1 | 8/2008 | Marentis |
| 2008/0198231 A1 | 8/2008 | Ozdemir et al. |
| 2008/0209342 A1 | 8/2008 | Taylor et al. |
| 2008/0222565 A1 | 9/2008 | Taylor et al. |
| 2008/0224862 A1 | 9/2008 | Cirker |
| 2008/0242945 A1 | 10/2008 | Gugliotti et al. |
| 2008/0250800 A1 | 10/2008 | Wetzel |
| 2008/0279420 A1 | 11/2008 | Masticola et al. |
| 2008/0280275 A1 | 11/2008 | Collopy |
| 2008/0303658 A1 | 12/2008 | Melker et al. |
| 2008/0306985 A1 | 12/2008 | Murray et al. |
| 2008/0320552 A1 | 12/2008 | Kumar et al. |
| 2009/0001181 A1 | 1/2009 | Siddaramanna et al. |
| 2009/0024944 A1 | 1/2009 | Louch et al. |
| 2009/0065596 A1 | 3/2009 | Seem et al. |
| 2009/0083120 A1 | 3/2009 | Strichman et al. |
| 2009/0096791 A1 | 4/2009 | Abshear et al. |
| 2009/0125337 A1 | 5/2009 | Abri |
| 2009/0125825 A1 | 5/2009 | Rye et al. |
| 2009/0144023 A1 | 6/2009 | Seem |
| 2009/0157744 A1 | 6/2009 | McConnell |
| 2009/0160673 A1 | 6/2009 | Cirker |
| 2009/0322782 A1 | 12/2009 | Kimchi et al. |
| 2010/0048167 A1 | 2/2010 | Chow et al. |
| 2010/0058248 A1 | 3/2010 | Park |
| 2010/0064001 A1 | 3/2010 | Daily |
| 2010/0070089 A1 | 3/2010 | Harrod et al. |
| 2010/0073162 A1 | 3/2010 | Johnson et al. |
| 2010/0123560 A1 | 5/2010 | Nix et al. |
| 2010/0134296 A1 | 6/2010 | Hwang |
| 2010/0156628 A1 | 6/2010 | Ainsbury et al. |
| 2010/0156630 A1 | 6/2010 | Ainsbury |
| 2010/0188228 A1 | 7/2010 | Hyland |
| 2010/0223198 A1 | 9/2010 | Noureldin et al. |
| 2010/0249955 A1 | 9/2010 | Sitton |
| 2010/0286937 A1 | 11/2010 | Hedley et al. |
| 2010/0318200 A1 | 12/2010 | Foslien et al. |
| 2010/0324962 A1 | 12/2010 | Nesler et al. |
| 2011/0010654 A1 | 1/2011 | Raymond et al. |
| 2011/0057799 A1 | 3/2011 | Taneff |
| 2011/0077779 A1 | 3/2011 | Fuller et al. |
| 2011/0083094 A1 | 4/2011 | Laycock et al. |
| 2011/0087988 A1 | 4/2011 | Ray et al. |
| 2011/0112854 A1 | 5/2011 | Koch et al. |
| 2011/0126111 A1 | 5/2011 | Gill et al. |
| 2011/0154426 A1 | 6/2011 | Doser et al. |
| 2011/0161124 A1 | 6/2011 | Lappinga et al. |
| 2011/0169646 A1 | 7/2011 | Raichman |
| 2011/0184563 A1 | 7/2011 | Foslien et al. |
| 2011/0202467 A1 | 8/2011 | Hilber et al. |
| 2011/0273298 A1 | 11/2011 | Snodgrass et al. |
| 2011/0291841 A1 | 12/2011 | Hollock et al. |

(56) References Cited

U.S. PATENT DOCUMENTS

| | | |
|---|---|---|
| 2011/0298301 A1 | 12/2011 | Wong et al. |
| 2011/0316703 A1 | 12/2011 | Butler et al. |
| 2011/0320054 A1 | 12/2011 | Brzezowski |
| 2012/0022700 A1 | 1/2012 | Drees et al. |
| 2012/0039503 A1 | 2/2012 | Chen et al. |
| 2012/0062382 A1 | 3/2012 | Taneff |
| 2012/0066168 A1 | 3/2012 | Fadell et al. |
| 2012/0075464 A1 | 3/2012 | Derenne et al. |
| 2012/0109988 A1 | 5/2012 | Li et al. |
| 2012/0112883 A1 | 5/2012 | Wallace et al. |
| 2012/0131217 A1 | 5/2012 | Delorme et al. |
| 2012/0158185 A1 | 6/2012 | El-Mankabady et al. |
| 2012/0216243 A1 | 8/2012 | Gill et al. |
| 2012/0224057 A1 | 9/2012 | Gill et al. |
| 2012/0259466 A1 | 10/2012 | Ray et al. |
| 2012/0262472 A1 | 10/2012 | Garr et al. |
| 2012/0272146 A1 | 10/2012 | D'souza et al. |
| 2012/0276517 A1 | 11/2012 | Banaszuk et al. |
| 2012/0291068 A1 | 11/2012 | Khushoo et al. |
| 2012/0303652 A1 | 11/2012 | Tseng |
| 2012/0310418 A1 | 12/2012 | Harrod et al. |
| 2013/0055132 A1 | 2/2013 | Foslien |
| 2013/0060794 A1 | 3/2013 | Puttabasappa et al. |
| 2013/0082842 A1 | 4/2013 | Balazs et al. |
| 2013/0086152 A1 | 4/2013 | Hersche et al. |
| 2013/0091631 A1 | 4/2013 | Hayes et al. |
| 2013/0110295 A1 | 5/2013 | Zheng et al. |
| 2013/0169681 A1 | 7/2013 | Rasane et al. |
| 2013/0184880 A1 | 7/2013 | McMahon |
| 2013/0187775 A1 | 7/2013 | Marsden et al. |
| 2013/0204570 A1 | 8/2013 | Mendelson et al. |
| 2013/0229276 A1 | 9/2013 | Hunter |
| 2013/0268293 A1 | 10/2013 | Knudson et al. |
| 2013/0289774 A1 | 10/2013 | Day et al. |
| 2014/0032157 A1 | 1/2014 | Khiani |
| 2014/0040998 A1 | 2/2014 | Hsieh |
| 2014/0046490 A1 | 2/2014 | Foslien et al. |
| 2014/0046722 A1 | 2/2014 | Rosenbloom et al. |
| 2014/0058539 A1 | 2/2014 | Park |
| 2014/0079282 A1 | 3/2014 | Marcheselli et al. |
| 2014/0167917 A2 | 6/2014 | Wallace et al. |
| 2014/0207291 A1 | 7/2014 | Golden et al. |
| 2014/0292518 A1 | 10/2014 | Wildman et al. |
| 2014/0307076 A1 | 10/2014 | Deutsch |
| 2014/0309757 A1 | 10/2014 | Le Sant et al. |
| 2014/0316582 A1 | 10/2014 | Berg-Sonne et al. |
| 2014/0320289 A1 | 10/2014 | Raichman |
| 2014/0342724 A1 | 11/2014 | Hill et al. |
| 2015/0025329 A1 | 1/2015 | Amarasingham et al. |
| 2015/0032264 A1 | 1/2015 | Emmons et al. |
| 2015/0056909 A1 | 2/2015 | Chien |
| 2015/0070174 A1 | 3/2015 | Douglas |
| 2015/0077258 A1 | 3/2015 | Nelson et al. |
| 2015/0113462 A1 | 4/2015 | Chen et al. |
| 2015/0153918 A1 | 6/2015 | Chen et al. |
| 2015/0161874 A1 | 6/2015 | Thyroff et al. |
| 2015/0167995 A1 | 6/2015 | Fadell et al. |
| 2015/0168949 A1 | 6/2015 | Hua et al. |
| 2015/0194043 A1 | 7/2015 | Dunn et al. |
| 2015/0198707 A1 | 7/2015 | Al-Alusi |
| 2015/0212717 A1 | 7/2015 | Nair et al. |
| 2015/0213222 A1 | 7/2015 | Amarasingham et al. |
| 2015/0213379 A1 | 7/2015 | Nair et al. |
| 2015/0216369 A1 | 8/2015 | Hamilton et al. |
| 2015/0253748 A1 | 9/2015 | Brun et al. |
| 2015/0281287 A1 | 10/2015 | Gill et al. |
| 2015/0310312 A1 | 10/2015 | Mongeon et al. |
| 2016/0061476 A1 | 3/2016 | Schultz et al. |
| 2016/0061477 A1 | 3/2016 | Schultz et al. |
| 2016/0061794 A1 | 3/2016 | Schultz et al. |
| 2016/0061795 A1 | 3/2016 | Schultz et al. |
| 2016/0063833 A1 | 3/2016 | Schultz et al. |
| 2016/0066067 A1 | 3/2016 | Schultz et al. |
| 2016/0110833 A1 | 4/2016 | Fix et al. |
| 2016/0116181 A1 | 4/2016 | Quitman et al. |
| 2016/0139067 A1 | 5/2016 | Grace |
| 2016/0253897 A1 | 9/2016 | Wildman et al. |
| 2016/0255516 A1 | 9/2016 | Hill et al. |
| 2016/0298864 A1 | 10/2016 | Ekolind et al. |
| 2016/0306934 A1 | 10/2016 | Sperry et al. |
| 2016/0314683 A1 | 10/2016 | Felch et al. |
| 2016/0328948 A1 | 11/2016 | Ferniany |
| 2016/0335731 A1 | 11/2016 | Hall |
| 2016/0367925 A1 | 12/2016 | Blackley |
| 2016/0371619 A1 | 12/2016 | Foster |
| 2017/0024986 A1 | 1/2017 | Austin |
| 2017/0193792 A1 | 7/2017 | Bermudez Rodriguez et al. |
| 2017/0256155 A1 | 9/2017 | Sengstaken, Jr. |
| 2017/0280949 A1 | 10/2017 | Wildman et al. |
| 2017/0294106 A1 | 10/2017 | Thyroff |
| 2017/0365024 A1 | 12/2017 | Koch et al. |
| 2018/0004178 A1 | 1/2018 | Haines et al. |
| 2018/0016773 A1 | 1/2018 | Chandler et al. |
| 2018/0113897 A1 | 4/2018 | Donlan et al. |
| 2018/0151054 A1 | 5/2018 | Pi |
| 2018/0218591 A1 | 8/2018 | Easter |
| 2018/0293038 A1 | 10/2018 | Meruva et al. |
| 2018/0301014 A1 | 10/2018 | Worral et al. |
| 2018/0313695 A1 | 11/2018 | Shim et al. |
| 2018/0365957 A1 | 12/2018 | Wright et al. |
| 2018/0375444 A1 | 12/2018 | Gamroth |
| 2019/0012607 A1 | 1/2019 | Holliday et al. |
| 2019/0051138 A1 | 2/2019 | Easter |
| 2019/0139395 A1 | 5/2019 | Rogachev et al. |
| 2019/0209719 A1 | 7/2019 | Andersen et al. |
| 2019/0295386 A1 | 9/2019 | Roberts |
| 2020/0009280 A1 | 1/2020 | Kupa et al. |
| 2020/0074836 A1 | 3/2020 | Kolavennu et al. |
| 2020/0090089 A1 | 3/2020 | Aston et al. |
| 2020/0146557 A1 | 5/2020 | Cheung et al. |
| 2020/0200420 A1 | 6/2020 | Nayak et al. |
| 2020/0327315 A1 | 10/2020 | Mullins |
| 2020/0364999 A1 | 11/2020 | Mullins |

FOREIGN PATENT DOCUMENTS

| | | |
|---|---|---|
| CN | 103110410 A | 5/2013 |
| CN | 103970977 A | 8/2014 |
| CN | 105116848 A | 12/2015 |
| CN | 108961714 A | 12/2018 |
| CN | 110009245 A | 7/2019 |
| CN | 110084928 A | 8/2019 |
| CN | 110118711 B | 12/2019 |
| CN | 110827457 A | 2/2020 |
| EP | 1669912 A1 | 6/2006 |
| EP | 2310981 A1 | 4/2011 |
| JP | 7085166 A | 3/1995 |
| JP | 11024735 A | 1/1999 |
| JP | 11317936 A | 11/1999 |
| JP | 2001356813 A | 12/2001 |
| JP | 2005242531 A | 9/2005 |
| JP | 2005311563 A | 11/2005 |
| JP | 110118711 A | 12/2019 |
| KR | 1172747 B1 | 8/2012 |
| KR | 101445367 B1 | 10/2014 |
| KR | 1499081 B1 | 3/2015 |
| WO | 9621264 A3 | 11/1996 |
| WO | 2004029518 A1 | 4/2004 |
| WO | 2005045715 A2 | 5/2005 |
| WO | 2008152433 A1 | 12/2008 |
| WO | 2008157755 A1 | 12/2008 |
| WO | 2009012319 A2 | 1/2009 |
| WO | 2009079648 A1 | 6/2009 |
| WO | 2010106474 A1 | 9/2010 |
| WO | 2011025085 A1 | 3/2011 |
| WO | 2011043732 A1 | 4/2011 |
| WO | 2011057173 A2 | 5/2011 |
| WO | 2011123743 A1 | 10/2011 |
| WO | 2013062725 A1 | 5/2013 |
| WO | 2013178819 A1 | 12/2013 |
| WO | 2014009291 A1 | 1/2014 |
| WO | 2014098861 A1 | 6/2014 |
| WO | 2014135517 A1 | 9/2014 |
| WO | 2016123536 A1 | 8/2016 |

(56) References Cited

FOREIGN PATENT DOCUMENTS

| | | | |
|---|---|---|---|
| WO | 2017057274 A1 | 4/2017 |
| WO | 2019046580 A1 | 3/2019 |
| WO | 2020024553 A1 | 2/2020 |
| WO | 2020248965 A1 | 12/2020 |

OTHER PUBLICATIONS

Proliphix, Inc., "Proliphix IP Devices: HTTP API," 28 pages, Jan. 23, 2006.
Proliphix, Inc., Remote Management User Guide, 12 pages, prior to Aug. 27, 2007.
Rogan et al., "Smart and Final Food Stores: A Case Study in Web Based Energy Information and Collection," Web Based Energy Information and Control Systems: Case Studies and Application, Chapter 6, p. 59-64, 2005.
Sharp, "Actius AL3DU 3D LC Display High Performance 3D Visualization," 2 pages, prior to Mar. 17, 2006.
So et al., "Building Automation on the Information Superhighway," ASHRAE (American Society of Heating Refrigerating, and Air Conditioning) Transactions, vol. 104, Part 2, pp. 176-191, 1998.
So et al., "Building Automation Systems on the Internet," Facilities vol. 15, No. 5/6, pp. 125-133, May/Jun. 1997.
Talon, "Raptor Controller," 6 pages, Oct. 2003.
Talon, "Workstation Software," 4 pages, Nov. 2002.
Trane, "System Programming, Tracer Summit Version 14, BMTW-SVP01D-EN," 623 pages, 2002.
Lucid Design Group, Inc., "Building Dashboard," 2 pages, Printed May 30, 2013.
"America's Largest Managed Security Services Provider Launches Comprehensive, Integrated Covid-19 Safety Program for Office Buildings and Suites," KastleSafeSpaces, 5 pages, May 11, 2020.
"Biometric Door Reader With Body Temperature Detection," Kintronics, 9 pages, accessed May 21, 2020.
"Body Surface Temperature Screening with Alarm Function TVS-200IS/TVS-500IS," Nippon Avionics Co., 3 pages, accessed May 21, 2020.
"BriefCam announces video analytics innovation for contact tracing, physical distancing, occupancy management and face mask detection," BriefCam LTD, 11 pages, Jun. 5, 2020.
"Thermal Imaging SmartPhone Can Be used For Temperature Screening of People," CAT, 3 pages, accessed Jul. 13, 2020.
"Contact Tracing Now Available on Identiv's Hirsch Velocity Access Control Platform," IDENTIV, 5 pages, May 21, 2020.
Silva et al., "Cough localization for the detection of respiratory diseases in pig houses," ScienceDirect, 7 pages, May 28, 2008.
Oey et al., "Evaluation of Isolation Compliance Using Real Time Video In Critical Care," North Shore University Hospital, 1 page, Oct. 9, 2015.
"Facial Attendace System With Temperature Screening Now In India," IANS, 5 pages, Mar. 19, 2020.
"Plan to Re-Open," EHIGH, 16 pages, accessed Jun. 13, 2020.
"How Smarter AI-Powered Cameras Can Mitigate the Spread of Wuhan Novel," AnyConnect, 22 pages, 2020.
"How to fight COVID-19 with machine learning," DataRevenue, 20 pages, accessed May 25, 2020.
"Inncontrol 5," Honeywell, 2 pages, Aug. 8, 2018.
"IP Door Access Control," Kintronics, 21 pages, 2014.
"Kogniz AI Health Response Platform," Kogniz, 9 pages, accessed May 21, 2020.
"Machine Learning Could Check If You're Social Distancing Properly at Work," MIT Technology Review, 7 pages, Apr. 17, 2020.
Punn et al., "Monitoring COVID-19 social distancing with person detection and tracking via fine-tuned YOLO v3 and Deepsort techniques," 10 pages, May 6, 2020.
"NEC launches dual face biometric and fever detection system for access control," Biometric Update, 4 pages, May 3, 2020.
"Remote temperature monitoring," Axis Communication, 10 pages, 2014.
"FebriEye-AI Based Thermal Temperature Screening System," vehant, 1 page, 2020.
"See The World In A New Way Hikvision Thermal Cameras," Hikvision, 12 pages, 2017.
Allain, "Trying out the iPhone Infrared Camera: The FLIR One," Wired, 15 pages, 2014.
Dasgupta, "Your voice may be able to tell you if you have Covid," Hindustan Times, 4 pages, Apr. 16, 2020.
Ganguty, "Gurugram-based startup Staqu has modified AI-powered JARVIS to battle coronavirus," Yourstory, 7 pages, Mar. 31, 2020.
"Energy Manager User Guide," Release 3.2, Honeywell, 180 pages, 2008.
"Fuzzy Logic Toolbox 2.1, Design and Stimulate Fuzzy Logic Systems," The MathWorks, 2 pages, May 2004.
"Junk Charts, Recycling Chartjunk as junk art," 3 pages, Oct. 2, 2006.
"Model Predictive Control Toolbox 2, Develop Internal Model-Based Controllers for Constrained Multivariable Processes," The MathWorks, 4 pages, Mar. 2005.
Honeywell, "Product Guide 2004," XP-002472407, 127 pages, 2004.
"Statistics Toolbox, for Use with Matlab," User's Guide Version2, The MathWorks, 408 pages, Jan. 1999.
"Vykon Energy Suite Student Guide," Tridium Inc., 307 pages, Mar. 3, 2006.
"Web Based Energy Information Systems for Energy Management and Demand Response in Commercial Buildings," California Energy Commission, 80 pages, Oct. 2003.
Andover Controls, Network News, vol. 2, No. 2, 8 pages, 1997.
Andover Controls World, 4 pages, Spring 1997.
Bell, Michael B. et al., "Early Event Detection-Results from A Prototype Implementation," AICHE Spring National Meeting, 15 pages, Apr. 2005.
Cadgraphics, "The Cadgraphics User's Guide," 198 pages, 2003.
Carrier Comfort Network CCN Web, "Web Browser User Interface to the Carrier Comfort Network," 2 pages, 2002.
Carrier Comfort Network CCN Web, Overview and Configuration Manual, 134 pages, Apr. 2006.
Carrier Comfort Network CCN Web, Product Data, 2 pages, Apr. 2006.
Carrier, "i-Vu Powerful and Intuitive Front End for Building Control," 2 pages, Aug. 2005.
Carrier, "i-Vu Web-Based Integrated Control System," 3 pages, 2005.
Carrier, Demo Screen Shots, 15 pages, prior to Aug. 27, 2007.
Carrier, i-Vu CCN 4.0, Owner's Guide, 20 pages, Jul. 2007.
Carrier, i-Vu CCN, 7 pages, 2007.
Chen, Tony. F., "Rank Revealing QR Factorizations," Linear Algebra and It's Applications, vol. 88-89, p. 67-82, Apr. 1987.
Circon, "i-Browse Web-Based Monitoring and Control for Facility Management," 2 pages, prior to Aug. 27, 2007.
Published Australian Application 2009904740, 28 pages, Application Filed on Sep. 29, 2009.
Echelon, "Energy Control Solutions with the i.Lon SmartServer," 4 pages, 2007.
Echelon, "i.Lon 100e3 Internet Server Models 72101R-300, 72101R-308, 72102R-300, 72103-R300 . . . " 5 pages, copyright 2002-2007.
Echelon, "i.Lon 100e3 Internet Server New Features," 15 pages, Sep. 2006.
Echelon, "i.Lon SmartServer," 5 pages, 2007.
Honeywell News Release, "Honeywell's New Sysnet Facilities Integration System for Boiler Plant and Combustion Safety Processes," 4 pages, Dec. 15, 1995.
Honeywell, "Excel Building Supervisor-Integrated R7044 and FS90 Ver. 2.0," Operator Manual, 70 pages, Apr. 1995.
Honeywell, "Introduction of the S7350A Honeywell WebPAD Information Appliance," Home and Building Control Bulletin, 2 pages, Aug. 29, 2000; Picture of WebPad Device with touch screen, 1 Page; and screen shots of WebPad Device, 4 pages.
Honeywell, Excel 15B W7760B Building Manager Release 2.02.00, Installation Instructions, 28 pages, Dec. 2004.
Honeywell, The RapidZone Solution, Excel 5000 Open System, Application Guide, 52 pages, Jan. 2004.

(56) References Cited

OTHER PUBLICATIONS http://pueblo.lbl.gov/~olken . . . , "Remote Building Monitoring and Operations Home Page," 5 pages, prior to Aug. 27, 2007.
http://www.commercial.carrier.com/commercial/hvac/productdescription . . . , "Carrier: i-Vu CCN," 1 page, printed Mar. 11, 2008.
http://www.commercial.carrier.com/commercial/hvac/productdescription . . . , "Carrier: 33CSCCNWEB-01 CCN Web Internet Connection to the Carrier Comfort Network," 1 page, printed Mar. 11, 2008.
http://www.docs.hvacpartners.com/idc/groups/public/documents/techlit/gs-controls-ivuccn.rtf, "Products," 5 pages, printed Jul. 3, 2007.
http://www.lightstat.com/products/istat.asp, Lightstat Incorporated, "Internet Programmable Communicating Thermostats," 1 page, printed Mar. 13, 2007.
http://www.sharpsystems.com/products/pc_notebooks/actius/rd/3d/, "Actius RD3D Desktop Replacement Notebook with Industry-Breakthrough 3D Screen," Sharp, 1 page, printed Jun. 16, 2005.
http://www2.sims.berkeley.edu/courses/is213/s06/projects/lightson;final.html, "Lights On A Wireless Lighting Control System," 11 pages, printed Mar. 22, 2007.
I.Lon 100e3 Internet Server, 1 page, prior to Aug. 27, 2007.
I.Lon, SmartServer, 2 pages, prior to Aug. 27, 2007.
I-stat, Demo Screen Shots, 9 pages, printed Mar. 13, 2007.
I-stat, The Internet Programmable Thermostat, 2 pages, prior to Aug. 27, 2007.
Ball, "Green Goal of 'Carbon Neutrality' Hits Limit," TheWall Street Journal, 7 pages, Dec. 30, 2008.
Johnson Controls, Network Integration Engine (NIE) 3 pages, Nov. 9, 2007.
Johnson Controls, Network Integration Engine (NIE), Product Bulletin, pp. 1-11, Jan. 30, 2008.
Kourti, "Process Analysis and Abnormal Situation Detection: From Theory to Practice," IEEE Control Systems Magazine, p. 10-25, Oct. 2002.
Matthew, "Action-Oriented Benchmarking, Using CEUS Date to Identify and Prioritize Efficiency Opportunities in California Commercial Buildings," 26 pages, Jun. 2007.
Morrison et al., "The Early Event Detection Toolkit," Honeywell Process Solutions, 14 pages, Jan. 2006.
Narang, "Webarc: Control and Monitoring of Building Systems Over the Web," 53 pages, May 1999.
Bocicor et al. "Wireless Sensor Network based System for the Prevention of Hospital Acquired Infections", arxiv.org, Cornell University Ithaca, NY 14853, May 2, 2017, XP080947042, (Abstract).
Shhedi et al., "Traditional and ICT Solutions for Preventing the Hospital Acquired Infection", 2015 20th International Conference on Control Systems and Computer Science, IEEE, May 27, 2015, pp. 867-873, XP033188038.
Extended European Search Report, EP application No. 20151295.1, pp. 13, dated May 26, 2020.
U.S. Appl. No. 14,109,496 filed Dec. 17, 2013.
www.geappliances.com/home-energy-manager/about-energy-monitors.htm, "Energy Monitor, Home Energy Monitors, GE Nucleus," 2 pages, printed Jan. 15, 2013.
www.luciddesigngroup.com/network/apps.php#homepage, "Lucid Design Group—Building Dashboard Network—Apps," 7 pages, Jan. 15, 2013.
Preuveneers et al., "Intelligent Widgets for Intuitive Interaction and Coordination in Smart Home Environments," IEEE Eighth International Conference on Intelligent Environments, pp. 157-164, 2012.
Wu et al., "A Web 2.0 Based Scientific Application Framework," 7 pages, prior to Jul. 24, 2014.
"4.0 Today's Activities, The Home Dashboard," CRBM info@hand website, 46 pages, prior to Apr. 25, 2013.
"Free Facilities Dashboards," eSight Energy Website, 2 pages, prior to Apr. 25, 2013.
Merton Building Controls, Gallery Prints, 7 pages, Dec. 19, 2013.
Carter, "Industrial Energy Management Dashboards Require a Toolkit," Cross Automation, 11 pages, Nov. 4, 2013.

U.S. Appl. No. 14/169,071, filed Jan. 30, 2014.
U.S. Appl. No. 14/169,083, filed Jan. 30, 2014.
U.S. Appl. No. 14/461,188, filed Aug. 15, 2014.
U.S. Appl. No. 14/482,607, filed Sep. 10, 2014.
e-homecontrols.com, "e-Home Controls Website," link to actual website no longer works, 1 page, prior to Dec. 19, 2013.
http://www.ccbac.com, "C&C (/)—Omniboard," 5 pages, Dec. 19, 2013.
http://www.domcontroller.com/en/, "DomController Home Automation Software—Control Anything from Anywhere," 11 pages, printed Jan. 6, 2015.
http://www.novar.com/ems-bas/opus-building-automation-system, "Novar OPUS BAS," 1 page, prior to Feb. 13, 2013.
Instituto Superior Tecnico, "A 3D Interactive Environment for Automated Building Control," Master's Dissertation, 120 pages, Nov. 2012.
Panduit Corp., "Enable a Building Automation with Panduit Enterprise Solutions," 4 pages, Nov. 2012.
"WEBs-AX Web-Enabled Building Solutions," sales brochure, Honeywell International Inc., Mar. 2009.
"Attune Advisory Services," press release, Honeywell International Inc., Mar. 20, 2012.
EnteliWEB product from Delta Controls, web pages retrieved on May 9, 2013 from http://deltacontrols.com/products/facilities-management/supervisory-software et seq. by the Internet Archive at web.archive.org.
"BACnet Protocol Implementation Conformance Statement" for enteliWEB, Delta Controls, Jul. 17, 2013.
Castle, "7 Software Platforms that Make Building Energy Management Easy," http://greentechadvocates.com/2012/11/28/7-software-platforms-that-make-building-energy-managment-easy/, Nov. 28, 2012.
EnteliWEB catalog sheet, Delta Controls, Inc., 2012.
EnteliWEB catalog sheet, Delta Controls., 2010.
"Intelligent Building Management Systems in Miami," Advanced Control Corp., Mar. 7, 2013.
"The Ohio State University," BACnet International Journal, vol. 5, p. 4, Jan. 2013.
Bobker et al., "Operational Effectiveness in Use of BAS," Proceedings of the 13th International Conference for Enhanced Building Operations, Oct. 8, 2013.
Castelo, "A 3D Interactive Environment for Automated Building Control," Elsevier, Nov. 8, 2012.
"Creston Special Report: How Intelligent building management solutions are reducing operational costs," Creston, 2012.
"Building Automation Software Solutions," Iconics, 2013.
Lacey, "The Top 10 Software Vendors Connecting Smart Buildings to the Smart Grid," http://www.greentechmedia.com/articles/read/the-top-10-companies-in-enterprise-smart-grid, Jul. 18, 2013.
"NiagraAX Product Model Overview," Tridium, Inc., 2005.
"An Overview of NiagraAX: A comprehensive software platform designed to create smart device applications," Tridium, Inc., 2005.
"Phoenix Controls Portal," Phoenix Controls, Inc., 2013.
Quirk, "A Brief History of BIM," Arch Daily, Dec. 7, 2012.
Samad et al., "Leveraging the Web: A Universal Framework for Building Automation," Proceedings of the 2007 American Control Conference, Jul. 11, 2007.
Sinha et al., "9 Key attributes of energy dashboards and analytics tools," https://www.greenbiz.com/blog/2013/08/28/9-key-attributes-energy-dashboards-and=analytics-tools, Aug. 28, 2013.
Sinopoli, "Dashboards For Buildings," http://www/automatedbuildings.com/news/dec.10/articles/sinopoli/101119034404sinopoli.html, Dec. 2010.
Sinoploi, "Modeling Building Automation and Control Systems," http://www.automatedbuildings.com/news/jun13/articles/sinopoli/130521122303sinopoli.html, Jun. 2013.
Zito, "What is Tridium Part 1," http://blog.buildingautomationmonthly.com/what-is-tridium/, May 12, 2013.
Zito, "What is Tridium Part 2," http://blog.buildingautomationmonthly.com/tridium-part-2/, Sep. 10, 2013.
Search Report and Written Opinion from related International PCT Application No. PCT/US2018/025189 dated Jul. 17, 2018 (12 pages).

(56) References Cited

OTHER PUBLICATIONS

"Data analytics and smart buildings increase comfort and energy efficiency", https://www.microsoft.com/itshowcase/Article/Content/845/Data-analytics-and-smart-buildings-increase-comfort-and-energy-efficiency, Dec. 19, 2016, 8 pages.

Donnelly, "Building Energy Management: Using Data as a Tool", http://www.buildingefficiencyinitiative.org/sites/default/files/legacy/InstituteBE/media/Library/Resources/Existing-Building-Retrofits/Using-Building-Data-as-a-Tool.pdf, Oct. 2012, 9 pages.

"ASHRAE Dashboard Research Project," 29 pages, Aug. 28, 2008.

Awiros: "Awiros Social Distancing and Face Mask Detection Apps Demo," May 6, 2020, XP55892197, Retrieved from the Internet: URL:https://www.youtube.com/watch?v=JHVKhIxLt68 [retrieved on Feb. 15, 2022] (2 pgs).

Empiricai: "Workplace Safety Analytics System—Social Distancing—Mask Detection—PPE Detection," Jun. 12, 2020, XP55892198, Retrieved from the Internet: URL: https://ww.youtube.com/watch?v=EdUksxjtgGc [retrieved on Feb. 15, 2022] (2 pgs).

Aioty: "Face Mask Detection and Social Distancing Detection System Using Artificial Intelligence," Apr. 20, 2022, XP55892199, Retrieved from the Internet: URL:https://www.youtube.com/watch?v=OPzrl7LsGAY [retrieved on Feb. 15, 2022] (2 pgs).

Extended European Search Report, EP Application No. 21177510.1, dated Mar. 14, 2022 (17 pgs).

Partial European Search Report, EP Application No. 21177510.1, dated Nov. 23, 2021 (17 pages).

Canadian Office Action, Canadian Patent Office, CA Application No. 3,120,436, dated Sep. 28, 2022 (4 pgs).

\* cited by examiner

USING SMART OCCUPANCY DETECTION AND CONTROL IN BUILDINGS TO REDUCE DISEASE TRANSMISSION

This is a continuation of co-pending U.S. patent application Ser. No. 16/907,044, filed Jun. 19, 2020, and entitled "USING SMART OCCUPANCY DETECTION AND CONTROL IN BUILDINGS TO REDUCE DISEASE TRANSMISSION", which is incorporated herein by reference.

TECHNICAL FIELD

The present disclosure relates generally to facility management systems, and more particularly to systems and methods for reducing risk of disease spread among occupants of a building.

BACKGROUND

Infectious diseases can spread through person to person contact, touching of contaminated surfaces, exposure to air borne pathogens, as well as other transmission mechanisms. What would be desirable are systems and methods to help limit the spread of a disease among occupants of a building.

SUMMARY

The present disclosure relates generally to systems and methods for reducing risk of disease spread among occupants of a building. In one example, a method includes tracking occupancy within a building that includes a plurality of building spaces, with each building space including an access point that allows access to the building space. Each building space includes one or more sensors that provide a signal when a person passes through the access point to the building space. A signal is received from a sensor each time a person passes through an access point corresponding to a building space of the plurality of building spaces of the building. The signal is identified as either indicating a person entering or exiting the building space of the plurality of building spaces. An occupancy count is maintained for each of the building spaces of the plurality of building spaces by incrementing the occupancy count when the signal indicates a person entering the building space and decrementing the occupancy count when the signal indicates a person exiting the building space. A determination is made as to whether the occupancy count for any of the building spaces of the plurality of building spaces has reached a threshold for the corresponding building space. Action is taken in response to determining that the occupancy count for any of the building spaces of the plurality of building spaces has reached the threshold for that particular building space.

In some cases the access point may function as a virtual fence or gate. The virtual fence may allow the system to maintain an accurate count of the occupants that are currently in the space without having to outfit sensors throughout the space. The lack of sensors throughout the space may also help increase the privacy of the occupants while in the space.

In another example, a system tracks occupancy within a building having a plurality of building spaces. The system includes a plurality of visible light sources distributed throughout each of at least some of the plurality of building spaces of the building, wherein each of the plurality of visible light sources is associated with (or has) a corresponding occupancy sensor, wherein when occupancy is detected, the corresponding visible light source is turned on, and when occupancy is not detected, the corresponding visible light source is turned off. A controller is operatively coupled to at least some of the occupancy sensors and is configured to monitor the occupancy sensors to infer an occupancy distribution in each of the at least some of the plurality of building spaces of the building. The controller is configured to compare the occupancy distribution in each of the at least some of the plurality of building spaces of the building with a corresponding occupancy distribution threshold and take action in response to determining that the occupancy distribution in one or more of the at least some of the plurality of building spaces of the building exceeds the corresponding occupancy distribution threshold.

In another example, a system disinfects a space within a building that includes a plurality of building spaces. The system includes a plurality of visible light sources distributed throughout each of at least some of the plurality of building spaces of the building, wherein each of the plurality of visible light sources is associated with a corresponding occupancy sensor, wherein when occupancy is detected, the corresponding light is turned on, and when occupancy is not detected, the corresponding light is turned off. A plurality of disinfecting UV light sources are distributed throughout each of at least some of the plurality of building spaces of the building, wherein when activated, the plurality of UV light sources disinfect at least some surfaces in a corresponding building space. A controller is operatively coupled to at least some of the occupancy sensors and the plurality of UV light sources. The controller is configured to monitor the occupancy sensors to determine when one or more of the plurality of building spaces of the building are unoccupied, activate one or more of the UV light sources in one or more of the plurality of building spaces of the building that are determined to be unoccupied, and monitor the occupancy sensors to determine if one or more of the plurality of building spaces of the building where the one or more of the UV light sources were activated become re-occupied, and if so, deactivating the corresponding UV light sources.

The preceding summary is provided to facilitate an understanding of some of the innovative features unique to the present disclosure and is not intended to be a full description. A full appreciation of the disclosure can be gained by taking the entire specification, claims, figures, and abstract as a whole.

BRIEF DESCRIPTION OF THE FIGURES

The disclosure may be more completely understood in consideration of the following description of various examples in connection with the accompanying drawings, in which.

Figure 1:
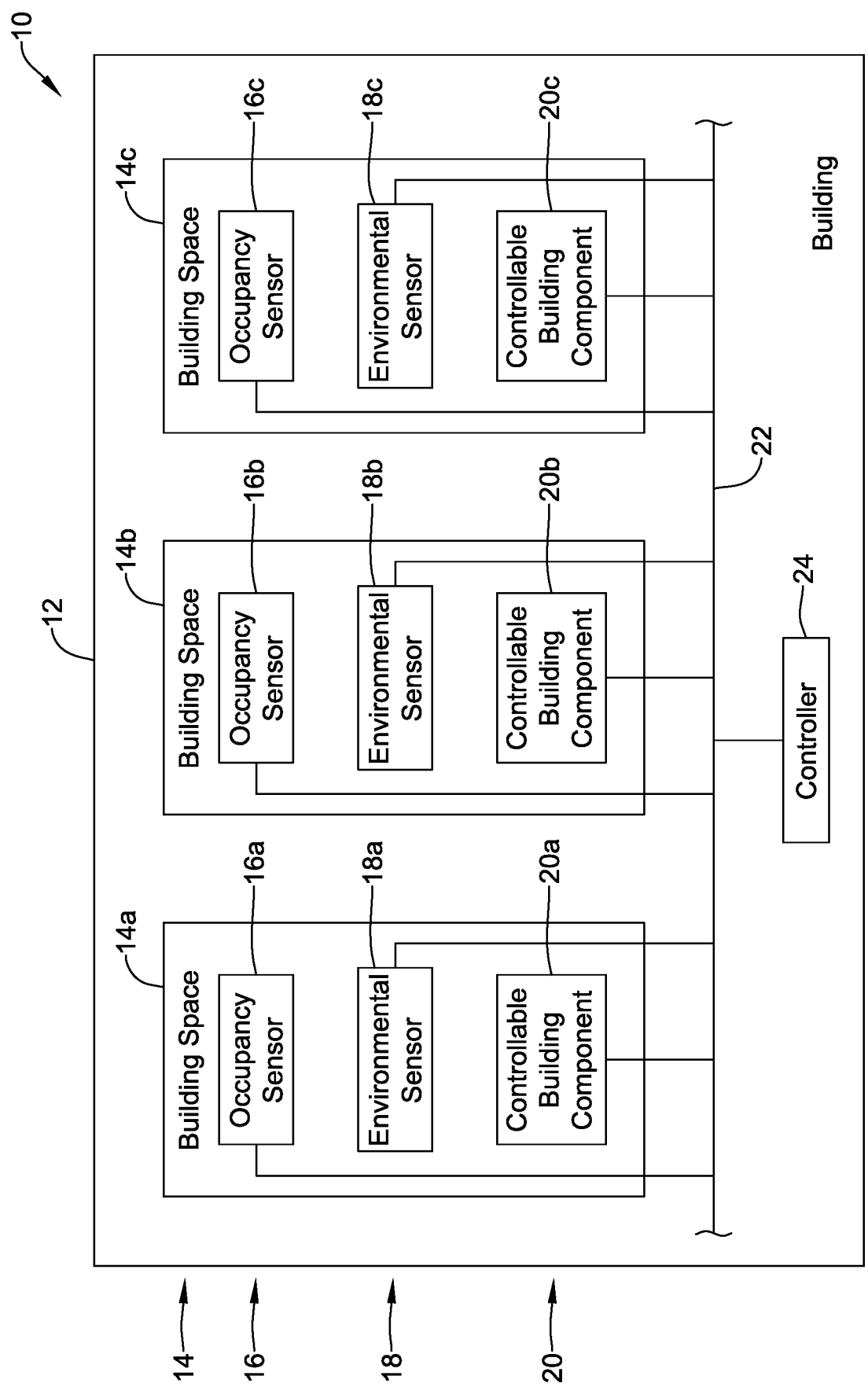
FIG. 1 is a schematic block diagram of an illustrative building management system.

While the disclosure is amenable to various modifications and alternative forms, specifics thereof have been shown by way of example in the drawings and will be described in detail. It should be understood, however, that the intention is not to limit the disclosure to the particular examples described. On the contrary, the intention is to cover all modifications, equivalents, and alternatives falling within the spirit and scope of the disclosure.

DESCRIPTION

The following description should be read with reference to the drawings, in which like elements in different drawings are numbered in like fashion. The drawings, which are not necessarily to scale, depict examples that are not intended to limit the scope of the disclosure. Although examples are illustrated for the various elements, those skilled in the art will recognize that many of the examples provided have suitable alternatives that may be utilized.

All numbers are herein assumed to be modified by the term "about", unless the content clearly dictates otherwise. The recitation of numerical ranges by endpoints includes all numbers subsumed within that range (e.g., 1 to 5 includes 1, 1.5, 2, 2.75, 3, 3.80, 4, and 5).

As used in this specification and the appended claims, the singular forms "a", "an", and "the" include the plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is contemplated that the feature, structure, or characteristic is described in connection with an embodiment, it is contemplated that the feature, structure, or characteristic may be applied to other embodiments whether or not explicitly described unless clearly stated to the contrary.

FIG. 1 is a schematic block diagram of an illustrative building management system 10. The illustrative building management system 10 is installed in a building 12 and may be considered as being configured to reduce the risk of pathogenic exposure within the building 12. The building 12 includes a number of building spaces 14 that are individually labeled as 14a, 14b, 14c. It will be appreciated that this is merely illustrative, as the building 12 will typically include a much greater number of building spaces 14 or zones. At least some of the building spaces 14 may periodically have one or more people within the building space 14. In some cases, the building 12 may be a hotel, and thus the building spaces 14 may be individually rentable guest rooms. The building 12 may be an office building, or a portion of an office building, and thus the building spaces 14 may be individual offices or work spaces. In some case, the disclosure may be applied to a cruise ship.

Each of the building spaces 14 includes one or more occupancy sensors 16, although only one occupancy sensor 16 is shown in each of the building spaces 14. The occupancy sensors 16 are individually labeled as 16a, 16b, 16c. At least some of the occupancy sensors 16 may be PIR sensors, mmWave sensors, motion sensors and/or microphones, for example. Some of the occupancy sensors 16 may be part of a security system of the building 12, for example. In some cases, some of the occupancy sensors 16 may be video cameras that are coupled with video analytics to detect the presence of one or more people, and hence determine occupancy. Occupancy detection may include detecting the presence of people, including counting people. Occupancy detection may also include behavioral indicators such as hand washing, signs of illness such as fever and coughing, spacing between people and the like.

Each of the building spaces 14 also include one or more environmental sensors 18, although only one environmental sensor 18 is shown in each of the building spaces 14. The environmental sensors 18 are individually labeled as 18a, 18b, 18c. The environmental sensors 18 may, for example, be sensors such as temperature sensors, humidity sensors, visible light sensors, UV sensors, particulate matter sensors (e.g. PM2.5, PM10), VOC sensors, airborne and waterborne pathogen sensors, CO sensors, $CO_2$ sensors, ozone sensors, and/or any other environmental suitable sensor. In some cases, some of the environmental sensors 18 may be considered as being Indoor Air Quality (IAQ) sensors. In some cases, one or more of the environmental sensors 18 may be disposed within a room thermostat within at least some of the building spaces 14.

In some cases, sensing environmental parameters may include sensing air pressure in general, and air pressure differentials across the building 12 in particular. It has been found that air pressure differentials can provide a general indication of air flow through the building 12. Air fill flow from an area of higher pressure to an area of lower pressure, for example. Measuring air pressure differentials can also provide an indication of how opening and closing windows and doors can influence air flow through the building 12, for example. Measuring air pressure differentials can also provide an indication of the impact of turning ventilation on or off, or turning ventilation rates up and down, among other HVAC capabilities. In some cases, controlled air flow is one of the key techniques highlighted by ASHRAE (American Society of Heating, Refrigerating and Air Conditioning Engineers) to control airborne pathogen transmission.

If a building space 14 is in a hospital operating room, for example, there is a desire to maintain an air pressure within the operating room that is higher than the air pressure in neighboring spaces. This can help to limit airborne pathogens from entering the operating room, as any air movement will tend to be from inside the operating room to outside of the operating room. If a building space 14 is not occupied, there may be a desire to reduce air flow in the duct(s) that provide conditioned air to the building space 14 in order to increase an amount of time that any airborne pathogens are exposed to UV light during a sanitizing process. These are just examples.

Each of the building spaces 14 includes one or more controllable building components 20, although only one controllable building component 20 is shown in each of the building spaces 14. Each of the controllable building components 20 may be considered as being configured to control environmental conditions within the building spaces 14 in order to reduce the likelihood of disease transmission among occupants of the building 12. At least some of the controllable building components 20 may include heating, ventilating and air conditioning system (HVAC) components such as heating sources, cooling sources, ventilation sources, humidifiers and dehumidifiers, as examples. At least some of the controllable building components 20 may include a disinfecting component. Examples of disinfecting components include sources of UV light that may be used to sanitize surfaces within the building space 14. UV light sources may also be used to disinfect components of an HVAC system, such as but not limited to disinfecting filters within the HVAC system. This may include cleaning filter media as well as electrostatic filters.

The UV light spectrum ranges from about 100 nanometers (nm) to about 400 nm. The UV light spectrum includes UV-A, which ranges from 315 nm to 400 nm. This UV light spectrum also includes UV-B, which ranges from 280 nm to 315 nm. UV-C, which ranges from 200 nm to 280 nm, is particularly effective for disinfecting. There is also Far-UVC, which ranges from 207 nm to 222 nm and thus is a subset of the UV-C light spectrum. Far-UVC is also particularly effective for disinfecting, and is believed to be safe for human skin and eyes. The UV light spectrum also includes VUV Far-UV, which ranges from 100 nm to 200 nm. In some cases, at least some of the controllable building components 20 may include a source of UV-C light that is configured to provide UV-C light for a period of time sufficient to disinfect surfaces within the building space 14. For example, it may take a period of time, such as 5 minutes, 10 minutes, 30 minutes, 1 hour, 2 hours, 3 hours or more, depending on a number of factors such as the intensity of the UV-C light source and the distance between the UV-C light source and the surfaces to be sanitized.

In the example shown, each of the occupancy sensors 16, each of the environmental sensors 18 and each of the controllable building components 20 are operably coupled with a building network 22. A controller 24 is operably coupled with the building network 22 such that the controller 24 is able to receive occupancy data from the occupancy sensors 16 and indoor air quality data from the environmental sensors 18. Accordingly, each of the one or more occupancy sensors 16 may be considered as providing occupancy signals over the building network 22. Similarly, each of the one or more environmental sensors 18 may be considered as providing air quality parameter signals over the building network 22. In some cases, the one or more environmental sensors 18 may provide a measurement of carbon dioxide concentration as a basic occupancy indicator. It will be appreciated that carbon dioxide concentration will increase as additional people are present within the building space 14, and will decrease as people leave the building space 14.

The controller 24 is also able to provide control signals to the controllable building components 20 via the building network 22. It is contemplated that the building network 22 may be a wired network, a wireless network or a combination of wired and wireless. It will be appreciated that while the controller 24 is shown as being located inside of the building 12, this is not required in all cases. In some instances, the controller 24 may itself be manifested within one or more computing devices that may be local to the building 12 or may be remote from the building 12. In some case, all or part of the controller 24 may be manifested within a cloud-based server.

In some instances, the controller 24 is configured to receive occupancy signals from the one or more occupancy sensors 16 over the building network 22 and to receive indoor air quality parameter signals from the one or more environmental sensors 18 over the building network 22. The controller 24 is configured to process the received occupancy signals and the received indoor air quality parameter signals (sometimes in combination) to determine whether action is needed to improve one or more environmental conditions within at least some of the plurality of building spaces 14 in order to reduce the likelihood of disease transmission among occupants of the building 12. Responsive to determining that action is needed, the controller 24 is configured to send control signals to one or more of controllable building components over the building network to improve one or more environmental conditions within at least some of the plurality of building spaces to reduce the likelihood of disease transmission among occupants of the building.

In some instances, the controller 24 is configured to process one or more of the received occupancy signals to identify a measure of compliance of one or more of the occupants of the building 12 with one or more predefined behavioral standards. In some cases, the occupancy signals may include locating sensors that can report a location of the one or more occupants of the building. The locating sensors may include, for example, Bluetooth or WiFi beacons that can be used to track an occupants phone's location in the building. It is contemplated that the locating sensor may be any locating sensor or system that is can identify a location of the one or more occupants in the building. In some cases, the occupancy signals may include video signals from a video camera or signals from an indoor radar sensor (e.g. mmWave sensor) that can be used to identify compliance of one or more of the occupants of the building 12 with one or more predefined behavioral standards. These are just examples.

One example of a predefined behavioral standard includes a social distancing standard. In some instances, maintaining a minimum distance between people may help prevent the transmission of disease. Social distancing can help reduce or limit the spread of disease from both symptomatic and asymptomatic carriers. The social distancing standard may be set to a particular physical distance that individuals should strive to maintain between themselves and other individuals, and may be determined at least in part upon the particular environment. People produce aerosols when talking, breathing, coughing and the like. If people stay far enough apart, these aerosols are able to drop out of the air before they reach another person who could inhale the aerosol and become infected. Relative humidity can impact how far an aerosol can travel. As an example, a social distancing standard may be set equal to 6 feet, or 12 feet.

Another example of a predefined behavioral standard includes a maximum people per building space standard. This may be equivalent to the maximum capacity for a particular building space 14, such as dictated by fire code. The maximum people per building space standard may dictate a reduced maximum capacity, particularly during times in which a particular pathogen is believed to be active. For example, the maximum people per building space standard during times in which pathogens are active may be set equal to fifty percent of the maximum occupancy dictated by fire code. The maximum people per building space standard may be set equal to twenty five percent the maximum occupancy dictated by fire code. These are just examples, as these numbers may vary depending on the communicability of a particular pathogen, the susceptibility of the people within the building 12 to the particular pathogen, and the like.

As another example, a predefined behavioral standard may include a hygiene standard. Examples of hygiene standards include whether individuals are wearing masks, particularly if the people are inside the building 12 and are not always complying with social distancing standards. Hygiene standards may also dictate whether a mask is required based upon how long two people may be in proximity to each other, as length of exposure can influence the degree or likelihood of pathogen transmission. The longer a person is exposed to a carrier, for example, the more of the pathogen that the person will have likely been exposed to and thus may now possess. Another example of a hygiene standard involves hand washing. This may be as simple as requiring that people wash their hands after using the bathroom. This may also include requiring people to wash their hands each time they move from one space to another space, or are about to eat or drink something, for example. Hand washing standards may specify a duration of time that hand washing is expected to last in order to be effective. For example, a hand washing time of twenty seconds is contemplated. Hygiene standards may also include specifying whether people are wearing gloves, as well as details regarding when, where and how the person is expected to wear gloves. A predefined behavioral standard may include ascertaining compliance with hygiene standards such as but not limited to wearing gloves, wearing masks, and hand washing.

In some instances, a predefined behavioral standard may include a symptoms standard. Depending on a suspected pathogen or a resulting disease, it will be appreciated that symptomatic individuals with the suspected pathogen or disease may have any of a variety of different symptoms. For example, various respiratory diseases may have symptoms that include coughing and/or sneezing. An elevated body temperature, better known as a fever, is also a common disease symptom as in many cases, the elevated body temperature is the result of the person's immune system trying to fight off the pathogen.

In some instances, a predefined behavioral standard may include a cleaning standard that is associated with a cleaning crew. This may include, for example, whether the correct area gets cleaned when that area is supposed to get cleaned. This may include whether the actual duration of the cleaning process meets or exceeds a cleaning time standard for that particular building space, for that particular cleaning crew and the like. Cleaning standards may also refer to automated cleaning and disinfecting processes, such as but not limited to an expected duration for exposing a surface or surfaces to UV-C light, for example. A disinfecting process may be set to last a particular length of time, but can be interrupted if a door is opened prematurely, for example. In some instances, the sensing controls may be integrated into a workflow application in order to provide a cleaning score or map that provides real-time insights to the cleaning staff. This may facilitate the cleaning staff being able to identify and take care of any missed spots, for example.

The controller 24 may be configured to process one or more of the received occupancy signals to identify a measure of a total number of occupants within one or more of the plurality of building spaces 14 of the building 12, and may use the measure of the total number of occupants within one or more of the plurality of building spaces 14 of the building 12 to determine whether action is needed. In some cases, the controller 24 may be configured to determine when action is needed by one or more persons to improve one or more environmental conditions within at least some of the plurality of building spaces 14 to reduce the likelihood of disease transmission among occupants of the building 12, and provide a notification. In some cases, the controller 24 may be configured to track occupancy over time, and thus may be able to learn when particular building spaces 14 are expected to remain empty.

In some instances, the controller 24 may be configured to determine that action is needed to maintain the indoor air quality when one or more indoor air quality parameters exceed a threshold for the corresponding one or more indoor air quality parameters, and in response, the controller 24 may be configured to output appropriate control signals requesting, for example, an increase in fresh air to the building space 14, an increase or decrease in a temperature and/or humidity level, and/or any other suitable change to the environment.

In some cases, the controller 24 may be configured to determine that action is needed to maintain the indoor air quality when one or more of the building spaces 14 have an indicated occupancy that is above a first occupancy threshold, and in response, the controller 24 may be configured to output appropriate control signals requesting, for example, an increase in fresh air to the building space 14, an increase or decrease in a temperature and/or humidity level, and/or any other suitable change to the environment. The controller 24 may be configured to determine that action is needed to maintain the indoor air quality when one or more of the building spaces 14 have an indicated occupancy that is at a second occupancy threshold, and in response, the controller 24 may be configured to output appropriate control signals indicating that no additional people are permitted in the one or more building spaces. The control signals may include instructions for an audio and/or visual warning that occupancy has reached the second threshold, and/or instructions to lock one or more doors in order to prevent additional people from entering the one or more building spaces.

In some instances, the controller 24 may be configured to process one or more of the received indoor air quality parameter signals to identify a measure of compliance with one or more air quality standards. Examples air quality standards include a relative humidity standard and a temperature standard. Other examples of air quality standards include a carbon dioxide ($CO_2$) standard, a carbon monoxide (CO) standard, a Particulate Matter (PM) standard, a pathogen concentration standard, a Volatile Organic Compound (VOC) standard, a H2CO standard.

Figure 2:
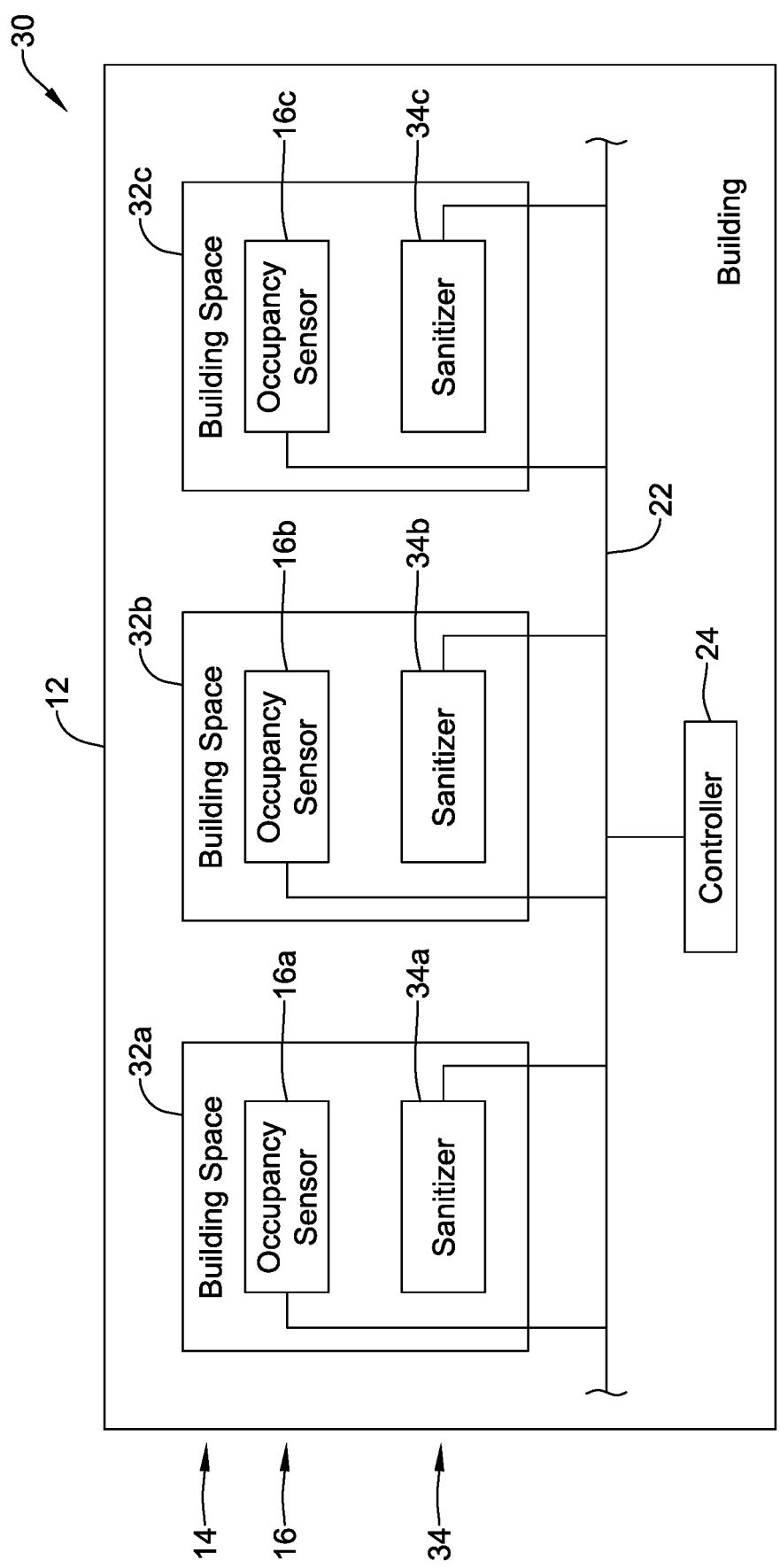
FIG. 2 is a schematic block diagram of an illustrative building management system.

FIG. 2 is a schematic block diagram of an illustrative building management system 30. The illustrative building management system 30 is shown as being installed in the building 12 and may be considered as being configured to reduce the risk of pathogenic exposure within the building 12. The building 12 includes a number of building spaces 32 that are individually labeled as 32a, 32ab, 32c. It will be appreciated that this is merely illustrative, as the building 12 will typically include a much greater number of building spaces 32 or zones. At least some of the building spaces 32 may periodically have one or more people within the building space 32. In some cases, at least some of the building spaces 32 may be considered as being examples of the building spaces 14. At least some of the building spaces 32 may include features ascribed to the building spaces 14. At least some of the building spaces 14 may include features ascribed to the building spaces 32.

In addition to the occupancy sensors 16, each of the building spaces 32 include one or more sanitizers 34, although only one sanitizer 34 is shown in each of the building spaces 32. The sanitizers are individually labeled as 34a, 34b, 34c. In some cases, the sanitizers 34 may each be sources of UV-C light. The sanitizers 34 may be considered as being positioned to sanitize surfaces within a corresponding building space 32. Disinfecting with other processes such as plasma and ionization is also contemplated. Each of the one or more occupancy sensors 16 may be considered as being positioned to detect occupancy within each of the plurality of building spaces 32, and may be considered as being operably connected to the building network 22. The controller 24 is configured to receive occupancy signals from the one or more occupancy sensors 16 and to process the occupancy signals to determine whether a particular building space 32 is due to be sanitized and is currently available to be sanitized. In some cases, determining whether the particular building space 32 is due to be sanitized is based at least in part upon how long it has been since that particular building space 32 was last sanitized and/or how many people have been in that particular building space 32 since it was last sanitized. In response to determining that the particular building space 32 is due to be sanitized and is currently available to be sanitized, the controller 24 outputs appropriate control signals to one or more of the one or more sanitizers 34 to proceed with sanitizing the particular building space 32.

Figure 3:
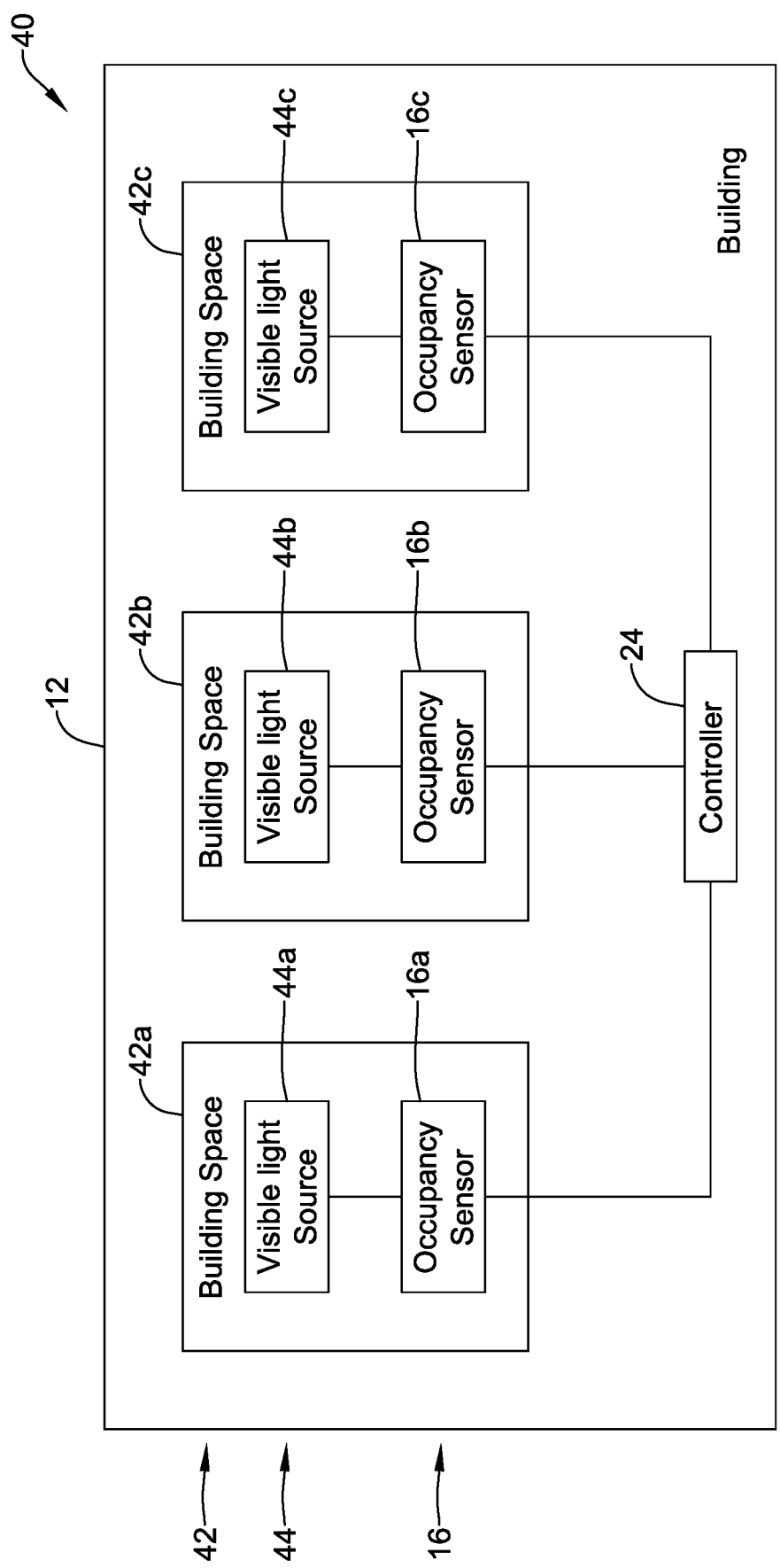
FIG. 3 is a schematic block diagram of an illustrative building management system.

FIG. 3 is a schematic block diagram of an illustrative building management system 40. The illustrative building management system 40 is shown as being installed in the building 12 and may be considered as being configured to disinfect spaces within the building 12. The building 12 includes a number of building spaces 42 that are individually labeled as 42a, 42ab, 42c. It will be appreciated that this is merely illustrative, as the building 12 will typically include a much greater number of building spaces 42 or zones. At least some of the building spaces 42 may periodically have one or more people within the building space 42. In some cases, at least some of the building spaces 42 may be considered as including features ascribed to the building spaces 14 and/or the building spaces 32. At least some of the building spaces 14 and 32 may include features ascribed to the building spaces 42.

In addition to the occupancy sensors 16, each of the building spaces 42 include one or more visible light sources 44, although only one visible light source 44 is shown in each of the building spaces 42. The visible light sources 44 are individually labeled as 44a, 44b, 44c. The visible light sources 44 may be considered as being distributed throughout each of at least some of the plurality of building spaces 42 of the building 12, wherein each of the plurality of visible light sources 44 is associated with a corresponding occupancy sensor 16, wherein when occupancy is detected, the corresponding visible light source 44 is turned on, and when occupancy is not detected, the corresponding visible light source 44 is turned off. In some instances, some of the occupancy sensors 16 may be integrated into a corresponding visible light source 44.

In some instances, the controller 24 may be configured to monitor the occupancy sensors 16 to infer an occupancy distribution in each of the at least some of the plurality of building spaces 42 of the building 12 and to compare the occupancy distribution in each of the at least some of the plurality of building spaces 42 of the building 12 with a corresponding occupancy distribution threshold. The controller 24 may be configured to take action in response to determining that the occupancy distribution in one or more of the at least some of the plurality of building spaces 42 of the building 12 exceeds the corresponding occupancy distribution threshold. Taking action may, for example, include providing an audio and/or visual warning that the occupancy distribution in one or more of the at least some of the plurality of building spaces 42 of the building 12 exceeds the corresponding occupancy distribution threshold. This is just an example. In some cases, the occupancy distribution threshold of one of the plurality of building spaces 42 may be different from the occupancy distribution threshold of another one of the plurality of building spaces 42.

Figure 4:
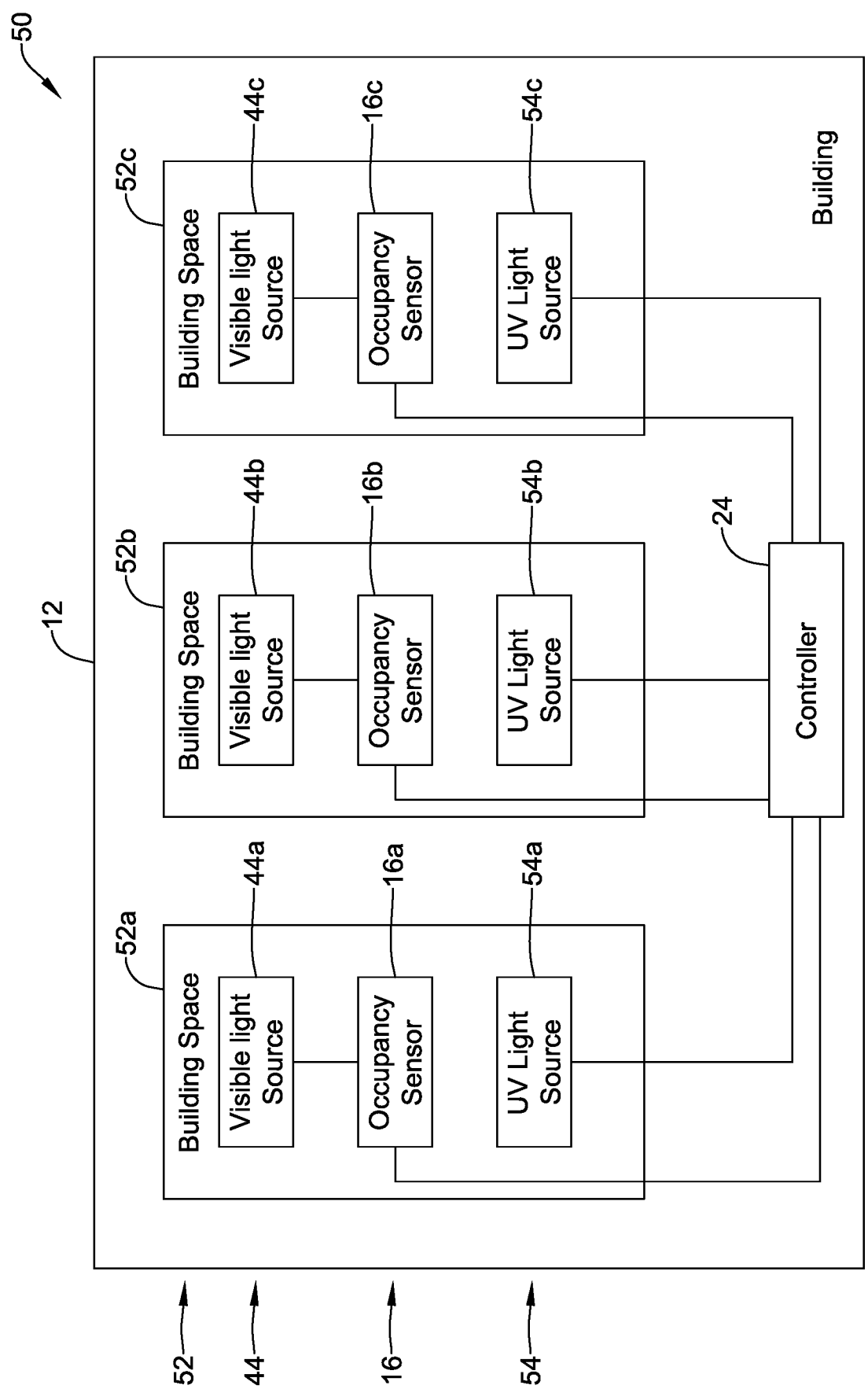
FIG. 4 is a schematic block diagram of an illustrative building management system.

FIG. 4 is a schematic block diagram of an illustrative building management system 50. The illustrative building management system 50 is shown as being installed in the building 12 and may be considered as being configured to disinfect spaces within the building 12. The building 12 includes a number of building spaces 52 that are individually labeled as 52a, 52ab, 52c. It will be appreciated that this is merely illustrative, as the building 12 will typically include a much greater number of building spaces 52 or zones. At least some of the building spaces 52 may periodically have one or more people within the building space 52. In some cases, at least some of the building spaces 52 may be considered as including features ascribed to the building spaces 14 and/or the building spaces 32 and/or the building spaces 42. At least some of the building spaces 14, 32 and 42 may include features ascribed to the building spaces 52.

In addition to the visible light sources 44 and the occupancy sensors 16, each of the building spaces 52 includes one or more UV light sources 54, although only one UV light source 54 is shown within each of the building spaces 52. The UV light sources 54 may be UV-C light sources, for example. The UV light sources 54 are individually labeled as 54a, 54b, 54c. Each of the visible light sources 44 are associated with a corresponding occupancy sensor 16 such that when occupancy is detected (by a particular occupancy sensor 16) the corresponding visible light source 44 is turned on, and when occupancy is not detected, the corresponding visible light source 44 is turned off.

The controller 24 is operably coupled to at least some of the occupancy sensors 16 and the plurality of UV light sources 54. In some instances, the controller 24 is configured to monitor the occupancy sensors 16 to determine when one or more of the plurality of building spaces 52 of the building 12 are unoccupied. The controller 24 may activate one or more of the UV light sources 54 in one or more of the plurality of building spaces 52 of the building 12 that are determined to be unoccupied. In some instances, the controller 24 may further determine when one or more of the plurality of building spaces 52 of the building 12 are unoccupied and are expected to remain unoccupied for at least a predetermined period of time based at least in part on a historical occupancy pattern.

In some cases, the controller 24 may activate the one or more UV light sources 54 for a predetermined period of time. The predetermined period of time may be user-adjustable, for example, by building management for the building 12. The predetermined period of time may be set when the system 50 is initially configured. The controller 24 may monitor the occupancy sensors 16 to determine if one or more of the plurality of building spaces 52 of the building 12 where the one or more of the UV light sources 54 were activated become re-occupied, and if so, deactivating the corresponding UV light sources 54. This can help prevent an individual walking into the building space 52 from being exposed to possibly damaging UV light. In some instances, the building space 52 may include a UVC sensor (not shown) that provides additional feedback to the controller 24 that an active UV light source is present, such that the controller 24 can provide a warning that the UV light source is active, and that the controller 24 can shut off the UV light source if occupancy is detected. In some cases, a signal from the UVC sensor can be taken into account when tracking disinfection statistics including how frequently and/or the duration of disinfecting processes.

Figure 5:
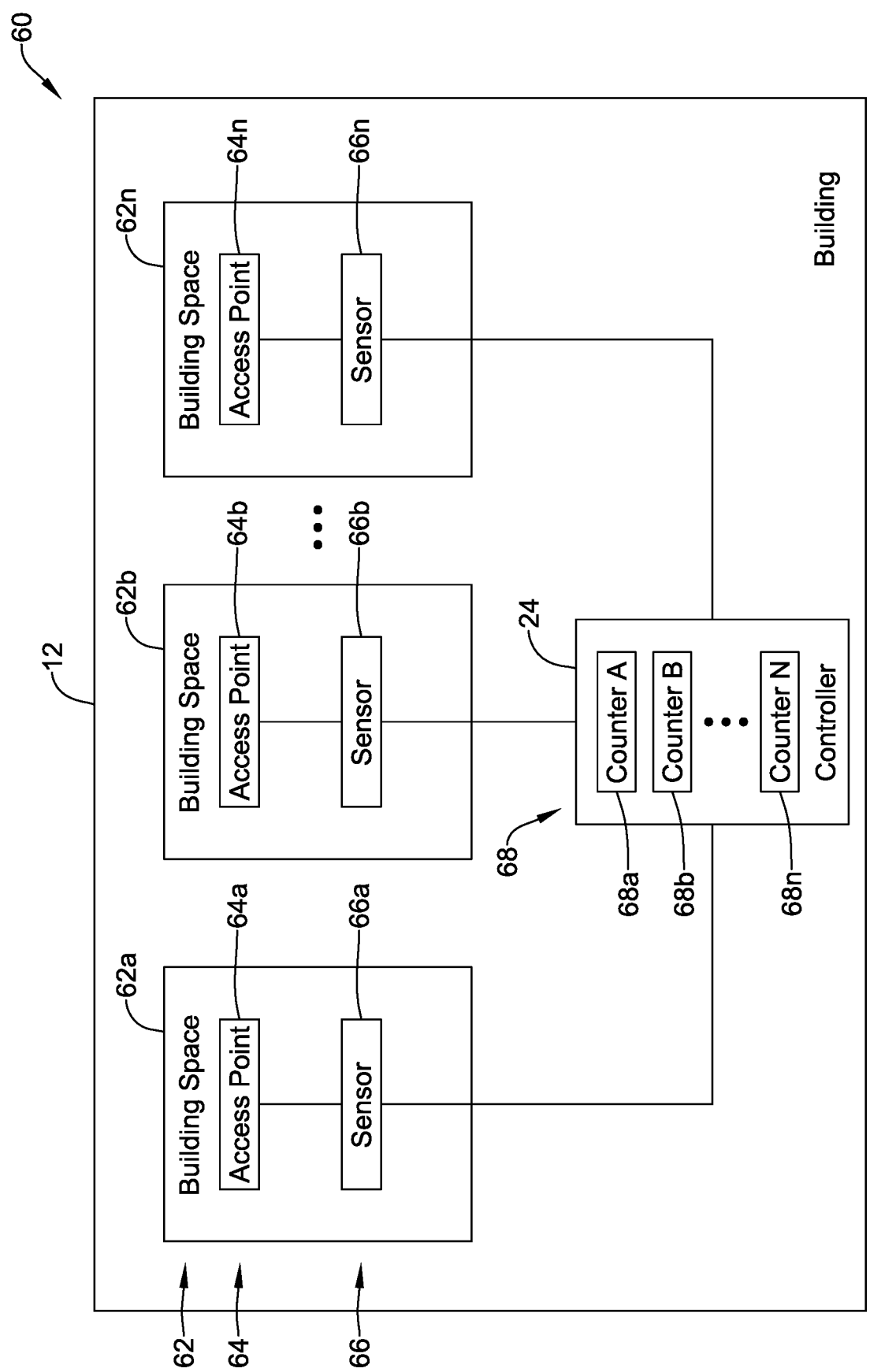
FIG. 5 is a schematic block diagram of an illustrative building management system.

FIG. 5 is a schematic block diagram of an illustrative building management system 60. The illustrative building management system 60 is shown as being installed within the building 12. The building 12 includes a number of building spaces 62 that are individually labeled as 62a, 62ab through 62n. At least some of the building spaces 62 may periodically have one or more people within the building space 62. In some cases, at least some of the building spaces 62 may be considered as including features ascribed to the building spaces 14 and/or the building spaces 32 and/or the building spaces 42 and/or the building spaces 52. At least some of the building spaces 14, 32, 42 and 52 may include features ascribed to the building spaces 62.

Each building space 62 includes at least one access point 64, although only one access point 64 is shown within each of the building spaces 62. The access points 64 are individually labeled as 64a, 64b through 64n. In some cases, a building space 62 may have more than one access point 64. In simplest terms, the access point 64 may be a physical or virtual door that allows people to enter and/or exit the building space 62. In some cases, the physical or virtual door can be closed to prevent additional people from passing through the access point 64 and entering the building space 62. An access point 64 may be a designated region of a hallway, elevator, lobby or the like, that can be considered as providing access to a particular building space 62.

Each building space 62 includes at least one sensor 66, although only one sensor 66 is shown in each of the building spaces 62. The sensors 66 are individually labeled as 66a, 66b through 66n. In some cases, there may be one sensor 66 that is associated with each of the access points 64. The sensors 66 may be configured to output a signal that indicates that someone has passed through an access point 66, either entering the building space 62 or exiting the building space 62. In some cases, at least some of the sensors 66 may include smart floor sensors that a person walks across. As the person walks across the smart floor sensor, a pressure signal is outputted that can indicate a direction of travel (i.e., into the building space 62 or out of the building space 62). The pressure signal may, for example, enable analysis that yields a shape or transient characteristics of a pressure input made by the person's foot, and thus a direction of travel can be determined. The smart floor sensor(s) can be embedded in a floor covering, such as but not limited to an area rug or mat. Thus, they can easily be used in a hallway to define an access point 64 (and corresponding sensor 66). In some cases, the smart floor sensor is large enough that a person passing through the access point 64 has to take multiple steps crossing the smart floor sensor. As a result, the direction of their travel is easily determined.

In some cases, at least some of the sensors 66 may include passive infrared (PIR) sensors. By placing two or more PIR sensors in the building space 62, it is possible to determine a direction of travel for a person passing through the access point 64. In some instances, at least some of the sensors 66 may include augmented PIR sensors that are configured to provide output signals that can indicate one or more of direction, distance and speed of a person traveling through the access point 64. In some cases, a building space 62 may include both a smart floor sensor and a PIR sensor as the sensors 66, such that a signal from one of the sensors 66 may be used as a check or confirmation of a signal from the other of the sensors 66. In some cases, at least some of the sensors 66 may include RFID card readers that can read an access card carried by a person without requiring the person to physically scan the access card. One or more of the sensors 66 may include a time of flight sensor that is based on a laser bean interruption, or a video camera. These are just some examples. With these and other types of sensors, the occupants can be granted frictionless access to a particular building space 62.

In some cases, Time of Flight (ToF) may be implemented as a technology that can count people moving through the access point 64. ToF can provide accurate people counting at low to medium traffic density, such as may occur when several people walk into a room at around the same time. ToF involves creating a pair of sensor zones, such as a front zone and a back zone. A person is detected as they cross through both the front zone and the back zone. In some instances, the sensors used for ToF measurements may be placed behind an optically opaque polymer panel. This can mean that ToF can be implemented unobtrusively, without people realizing that they are walking past a sensor, or even realizing that they are being counted.

In some instances, the controller 24 maintains a counter 68 for each of the access points 64. The controller 24 may include a counter 68a that corresponds to the sensor 66a, a counter 68b that corresponds to the sensor 66b, all the way through a counter 68n that corresponds to the sensor 66n. The appropriate counter 68 may be incremented in response to the controller 24 receiving an indication from a particular sensor 66 that a person has entered the particular building space 62 through that access point 64 and may be decremented in response to the controller 24 receiving an indication from a particular sensor 66 that a person has exited the particular building space 62 through that access point 64.

Once a particular counter 68 has reached a particular threshold, the controller 24 may take appropriate action. In some cases, taking action in response to the counter 68 reaching a threshold may include issuing an audio and/or visual warning that current occupancy within a particular building space 62 has reached the threshold for that particular building space 62. Taking action may, for example, include securing the access point 66 for the particular building space 62 such that people are allowed to exit the building space 62 but are not allowed to enter the building space 62 until the occupancy counter 68 for that particular building space 62 drops below the threshold. In some cases, taking action may include increasing an air ventilation rate for that building space 62.

Figure 6:
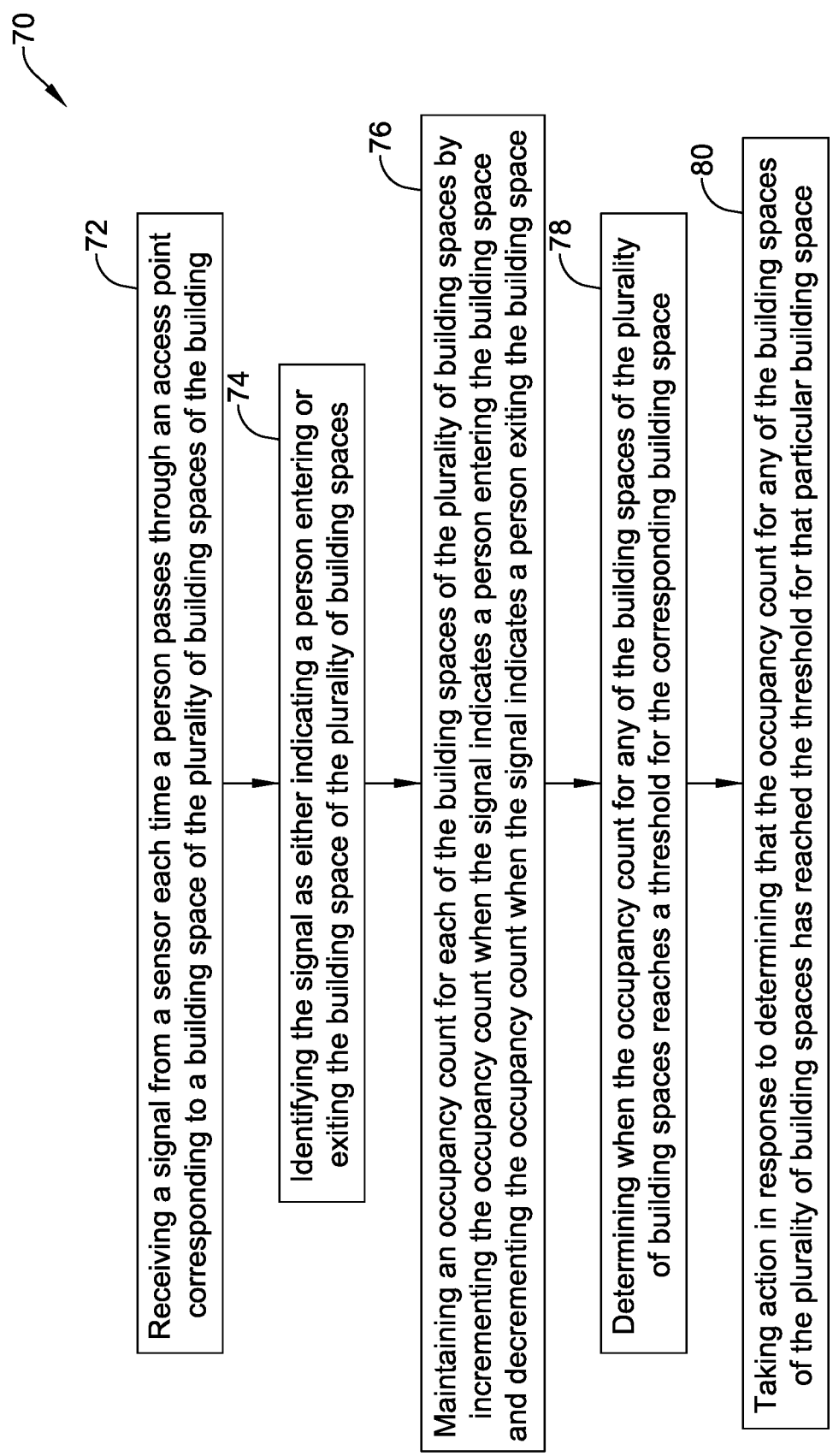
FIG. 6 is a flow diagram showing an illustrative method that may be carried out via the illustrative building management systems of FIGS. 1 through 5.

FIG. 6 is a flow diagram showing an illustrative method 70 for tracking occupancy within a building that includes a plurality of building spaces, with each building space including an access point that allows access to the building space and a sensor that provides a signal when a person passes through the access point. A signal is received from a sensor each time a person passes through an access point corresponding to a building space of the plurality of building spaces of the building, as indicated at block 72. The signal is identified as either indicating a person entering or exiting the building space of the plurality of building spaces, as indicated at block 74. An occupancy count is maintained for each of the building spaces of the plurality of building spaces by incrementing the occupancy count when the signal indicates a person entering the building space and decrementing the occupancy count when the signal indicates a person exiting the building space, as indicated at block 76. A determination may be made that the occupancy count for any of the building spaces of the plurality of building spaces has reached a threshold for the corresponding building space, as indicated at block 80.

In response to determining that the occupancy count for any of the building spaces of the plurality of building spaces has reached the threshold for that particular building space, action is taken, as indicated at block 80. Taking action may, for example, include issuing an audio and/or visual warning that current occupancy within a particular building space of the plurality of building spaces has reached the threshold for that particular building space. In some instances, taking action includes securing the access point for the particular building space of the plurality of building spaces such that people are allowed to exit but are not allowed to enter until the occupancy count for that particular building space drops below the threshold. Taking action can additionally or alternatively include increasing an air ventilation rate for the particular building space of the plurality of building spaces.

In some cases, the sensor associated with the access point of at least one of the building spaces of the plurality of building spaces may include a smart floor sensor embedded in a floor covering. The sensor associated with the access point of at least one of the building spaces of the plurality of building spaces may include a passive infrared (PIR) sensor. The sensor associated with the access point of at least one of the building spaces of the plurality of building spaces may include an RFID card reader that can read an access card carried by a person without requiring the person to physically scan the access card to provide frictionless access through the corresponding access point.

The sensor associated with the access point of at least one of the building spaces of the plurality of building spaces may include a video camera having a field of view that includes at least part of the corresponding access point, wherein video analytics are applied to identify the signal from the video camera as either indicating a person entering or exiting the building space of the plurality of building spaces. The video analytics may include identifying biometric identification. The video analytics may include identifying compliance with one or more behavioral thresholds such as but not limited to one or more of a social distancing compliance threshold, a hand hygiene compliance threshold and a Personal Protective Equipment (PPE) compliance threshold.

The access point may, for example, include one of a building entry, an emergency exit, a door or hall to a room or zone, an elevator, and a stair case. At least one of the access points may further include a health screening sensor for performing a health screen of a person passing through the access point, wherein the health screening sensor comprises one or more or a video camera, a thermal camera and a microphone.

Figure 7:
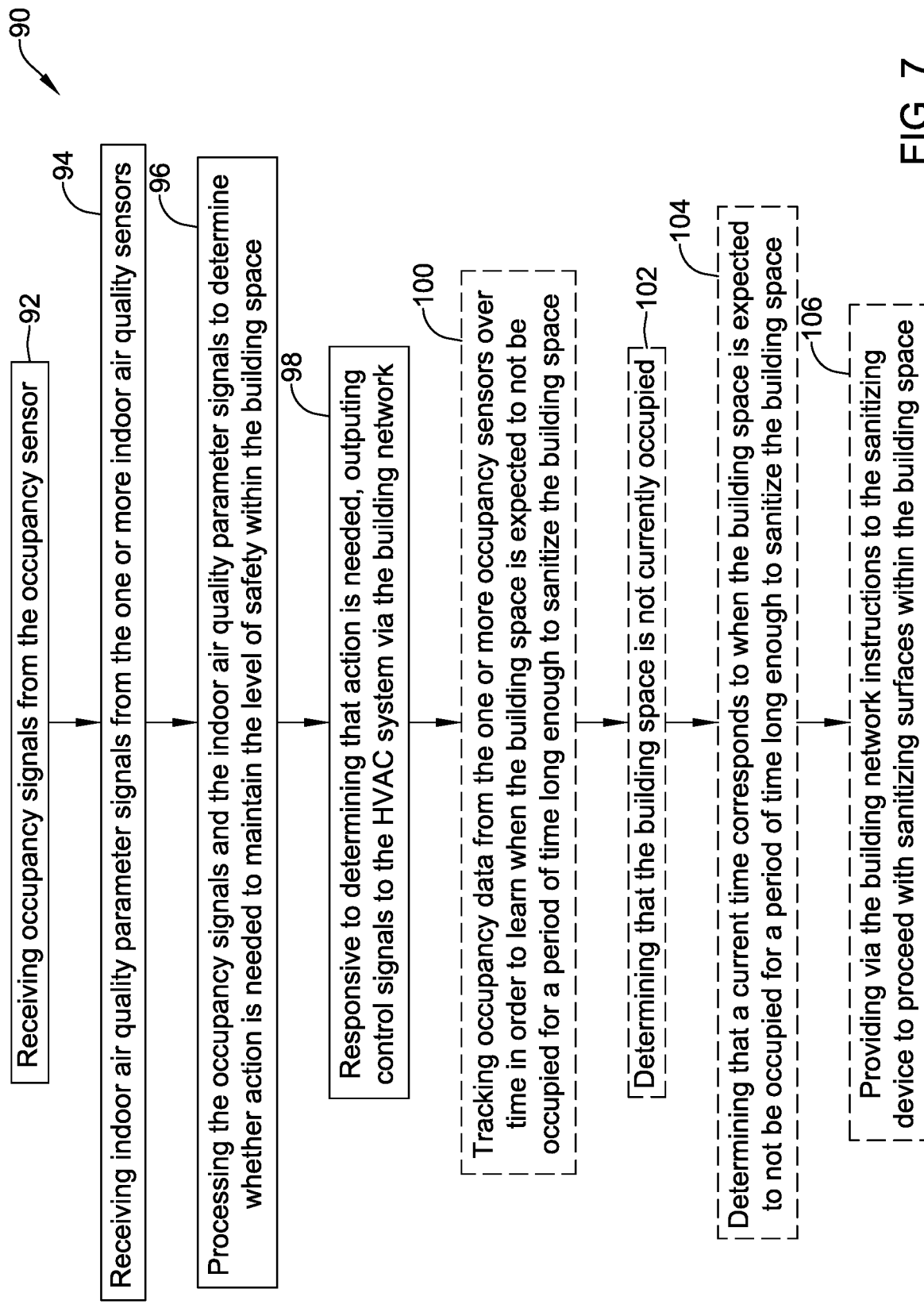
FIG. 7 is a flow diagram showing an illustrative method that may be carried out via the illustrative building management systems of FIGS. 1 through 5.

FIG. 7 is a flow diagram showing an illustrative method 90 of maintaining a level of occupant safety within a building having a building space, the building space including an occupancy sensor and one or more air quality sensors, the building space serviced by a heating, ventilating and air conditioning (HVAC) system, each of the sensors and the HVAC system operably coupled with a building network. Occupancy signals are received from the occupancy sensor, as indicated at block 92. Indoor air quality parameter signals are received from the one or more indoor air quality sensors, as indicated at block 94. The occupancy signals and the indoor air quality parameter signals are processed to determine whether action is needed to maintain the level of safety within the building space, as indicated at block 96. Responsive to determining that action is needed, control signals are outputted to the HVAC system via the building network, as indicated at block 98.

In some cases, the building space may be serviced by a sanitizing device. The method 90 may further include tracking occupancy data from the one or more occupancy sensors over time in order to learn when the building space is expected to not be occupied for a period of time long enough to sanitize the building space, as optionally indicated at block 100. A determination may be made that the building space is not currently occupied, as optionally indicated at block 102. A determination may be made that a current time corresponds to when the building space is expected to not be occupied for a period of time long enough to sanitize the building space, as optionally indicated at block 104. In some cases, and as optionally indicated at block 106, instructions may be provided via the building network to the sanitizing device to proceed with sanitizing surfaces within the building space. In some cases, a warning may be issued via the building network that the building space is currently being sanitized.

Figure 8:
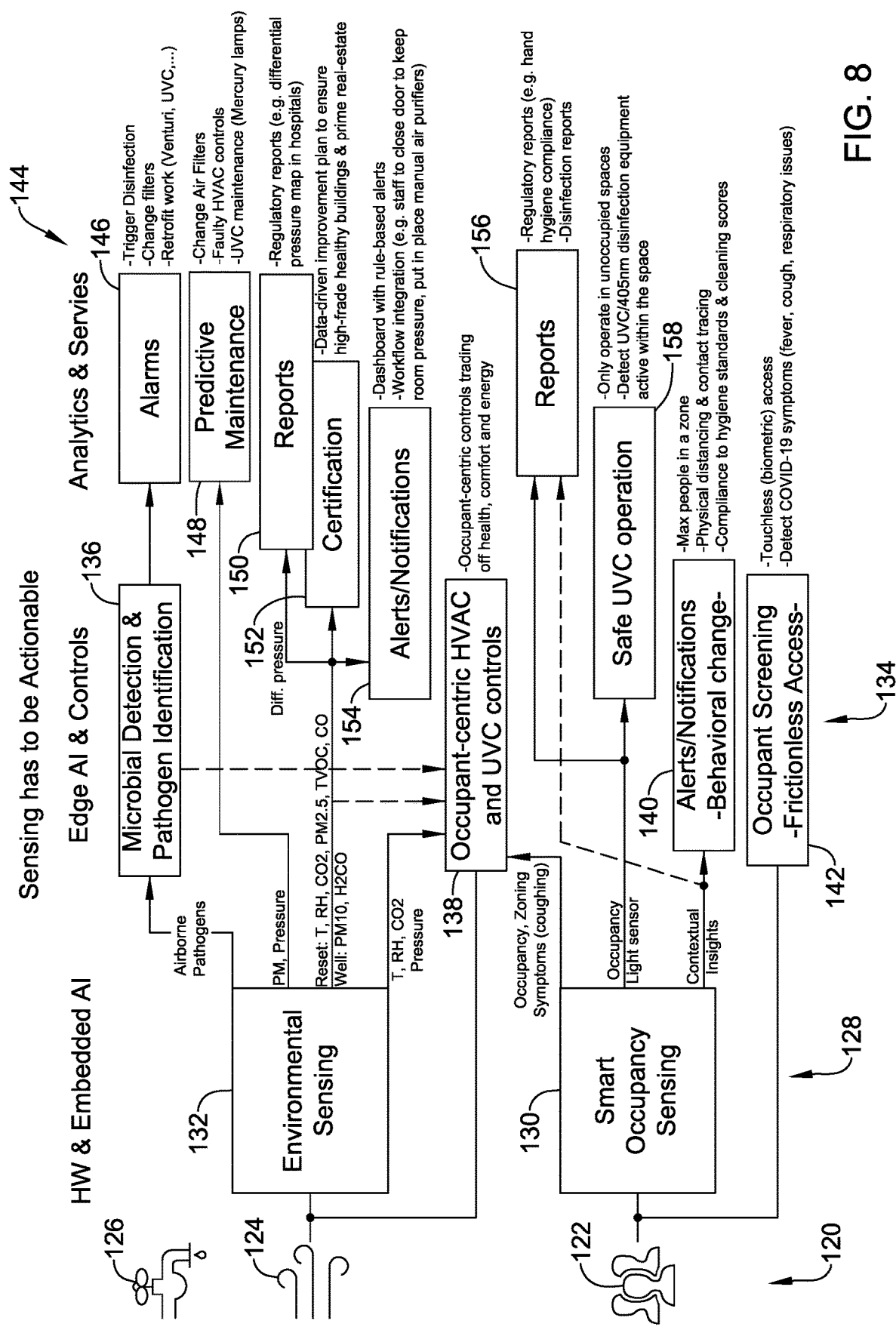
FIG. 8 is a schematic block diagram illustrating relationships between sensing and corresponding actions.

FIG. 8 is a schematic block diagram illustrating relationships between sensing and corresponding actions. On the far left are possible inputs 120. As shown, the possible inputs 120 may include people, as indicated by a people icon 122. The possible inputs 120 may include environmental conditions, as represented by a wind icon 124. In some cases, the possible inputs 120 may include a pathogen, as indicated by the pathogen icon 126. These possible inputs 120 may be sensed via a sensing section 128. The sensing section 128 may include a smart occupancy sensing block 130 and an environmental sensing block 132. Possible outputs from the smart occupancy sensing block 130 may include one or more of occupancy numbers for a zone, as well as possibly detected symptoms within the zone such as coughing. Possible outputs from the smart occupancy sensing block 130 may also include occupancy detection that might cause lighting to be turned on or off, for example. In some cases, a degree of hysteresis or a short delay may be implemented in order to prevent a possible situation in which the lights turn on and off while a person lingers in the doorway, for example, which can be hard on lighting equipment and may be uncomfortable for the person in the doorway. Even if hysteresis is implemented with respect to lighting control, the smart occupancy sensing block 130 may immediately report occupancy.

Possible outputs from the environmental sensing block 132 may include detection of airborne pathogens. Possible outputs from the environmental sensing block 132 may include any of a variety of different air quality parameters such as but not limited to particulate matter (PM), air pressure, temperature, relative humidity, carbon dioxide concentration, PM2.5, total volatile organic compound (TVOC) concentration, carbon monoxide concentration, H2CO (formaldehyde) concentration, and the like.

An actions section 134 includes a number of different possible actions. It will be appreciated that, as shown, the inputs to individual blocks within the actions section 134 (the possible outputs from the sensing section 128) can vary, depending on the specific actions block. For example, the actions section 134 includes a Microbial Detection and Pathogen Identification block 136 that receives sensed data pertaining to sensed airborne pathogens. The actions section 134 includes an Occupant-centric HVAC and UVC Controls block 138. As can be seen, the Occupant-centric HVAC and UVC Controls block 138 can receive a number of different inputs, including occupancy data from the Smart Occupancy Sensing block 130 and a number of air quality parameters from the Environmental Sensing block 132. The actions section 134 also includes an Alerts/Notifications block 140 and an Occupant Screening block 142. The Alerts/Notifications block 140 may output information pertaining to maximum allowed occupancy, physical distancing between people, contact tracing and compliance to hygiene standards. The Occupant Screening block 142 may output information related to touchless or biometric access and detecting symptoms of illness.

An analytics section 144 includes an Alarms block 146 and a Predictive Maintenance block 148. Illustrative outputs from the Alarms block 146 and the Predictive Maintenance block 148 are listed. A Reports block 150 and a Certification block 152 can output regulatory reports and data-driven improvement plans, respectively, as shown. An Alerts/Notifications block 154 can output information to a dashboard. A Safe UVC Operation block 158 confirms that UVC sterilization only occurs in unoccupied spaces.

Having thus described several illustrative embodiments of the present disclosure, those of skill in the art will readily appreciate that yet other embodiments may be made and used within the scope of the claims hereto attached. It will be understood, however, that this disclosure is, in many respects, only illustrative. Changes may be made in details, particularly in matters of shape, size, arrangement of parts, and exclusion and order of steps, without exceeding the scope of the disclosure. The disclosure's scope is, of course, defined in the language in which the appended claims are expressed.

What is claimed is:

1. A method of tracking occupancy within a building, the building including a plurality of building spaces, each building space of the plurality of building spaces including an access point that allows access to the building space and a sensor that provides a signal when a person passes through the access point, the method comprising:
   maintaining an occupancy count for each of the building spaces of the plurality of building spaces;
   determining when the occupancy count for any of the building spaces of the plurality of building spaces reaches a threshold for the corresponding building space; and
   taking action in response to determining that the occupancy count for any of the building spaces of the plurality of building spaces has reached the threshold for that particular building space, wherein taking action comprises controlling one or more building management systems of the building to alter one or more conditions of the particular building space to reduce a likelihood of disease transmission among occupants of the particular building space, including:
      altering the relative humidity of air in the particular building space relative to a current relative humidity so as to reduce the time a pathogen aerosol will remain in the air; and/or
      increasing the air temperature in the particular building space relative to a current air temperature.

2. The method of claim 1, further comprising:

receiving a signal from a Time of Flight (ToF) sensor each time a person passes through an access point corresponding to a building space of the plurality of building spaces of the building;

identifying the signal as either indicating a person entering or exiting the building space of the plurality of building spaces; and maintaining the occupancy count for each of the building spaces of the plurality of building spaces by incrementing the occupancy count when the signal indicates a person entering the building space and decrementing the occupancy count when the signal indicates a person exiting the building space.

3. The method of claim 1, wherein controlling the one or more building management systems of the building to alter one or more conditions of the particular building space to reduce the likelihood of disease transmission among occupants of the particular building space comprises controlling the one or more building management systems of the building to increase a fresh air ventilation rate to the particular building space.

4. The method of claim 3, wherein controlling the one or more building management systems of the building to alter one or more conditions of the particular building space to reduce the likelihood of disease transmission among occupants of the particular building space comprises controlling the access point for the particular building space such that people are allowed to exit the particular building space but are not allowed to enter until the occupancy count for that particular building space drops below the threshold.

5. The method of claim 1, wherein controlling the one or more building management systems of the building to alter one or more conditions of the particular building space to reduce the likelihood of disease transmission among occupants of the particular building space includes increasing the air temperature in the particular building space.

6. The method of claim 1, wherein controlling the one or more building management systems of the building to alter one or more conditions of the particular building space to reduce the likelihood of disease transmission among occupants of the particular building space includes increasing the relative humidity in the particular building space.

7. The method of claim 1, wherein controlling the one or more building management systems of the building to alter one or more conditions of the particular building space to reduce the likelihood of disease transmission among occupants of the particular building space comprises controlling the access point for the particular building space such that people are allowed to exit the particular building space but are not allowed to enter until the occupancy count for that particular building space drops below the threshold.

8. The method of claim 1, further comprising:

receiving a signal from sensor each time a person passes through an access point corresponding to a building space of the plurality of building spaces of the building;

identifying the signal as either indicating a person entering or exiting the building space of the plurality of building spaces; and maintaining the occupancy count for each of the building spaces of the plurality of building spaces by incrementing the occupancy count when the signal indicates a person entering the building space and decrementing the occupancy count when the signal indicates a person exiting the building space.

9. The method of claim 8, wherein the sensor comprises a smart floor sensor embedded in a floor covering.

10. The method of claim 8, wherein the sensor comprises a passive infrared (PIR) sensor.

11. The method of claim 8, wherein the sensor comprises an RFID card reader that can read an access card carried by a person without requiring the person to physically scan the access card to provide frictionless access through the access point.

12. The method of claim 8, wherein the sensor comprises a video camera having a field of view that includes at least part of access point, wherein video analytics are applied to identify whether a person is entering or exiting the building space of the plurality of building spaces.

13. The method of claim 12, wherein the video analytics include identifying compliance whether a person is complying with one or more of a social distancing metric and a Personal Protective Equipment (PPE) metric.

14. The method of claim 8, wherein the access point further comprises a health screening sensor for performing a health screen of a person passing through the access point, wherein the health screening sensor comprises one or more or a video camera, a thermal camera and a microphone.

15. A system for tracking occupancy within a building, the building including a plurality of building spaces, the system comprising:
  a plurality of visible light sources distributed throughout each of at least some of the plurality of building spaces of the building, wherein each of the plurality of visible light sources includes a corresponding occupancy sensor;
  a controller operatively coupled to at least some of the occupancy sensors, the controller configured to:
    monitor the occupancy sensors to infer an occupancy distribution within each of the at least some of the plurality of building spaces of the building;
    compare the occupancy distribution within each of the at least some of the plurality of building spaces of the building with a corresponding occupancy distribution threshold; and
    take action in response to determining that the occupancy distribution for any of the building spaces of the plurality of building spaces has reached the corresponding occupancy distribution threshold for that particular building space, wherein taking action comprises controlling an HVAC system of the building to alter one or more environmental conditions of the particular building space to reduce a likelihood of disease transmission among occupants of the particular building space.

16. The system of claim 15, wherein controlling the HVAC system of the building to alter one or more environmental conditions of the particular building space to reduce the likelihood of disease transmission among occupants of the particular building space comprises controlling the HVAC system of the building to increase a fresh air ventilation rate to the particular building space.

17. The system of claim 15, wherein controlling the HVAC system of the building to alter one or more environmental conditions of the particular building space to reduce the likelihood of disease transmission among occupants of the particular building space comprises controlling the HVAC system of the building to increase the air temperature in the particular building space.

18. The system of claim 15, wherein controlling the HVAC system of the building to alter one or more environmental conditions of the particular building space to reduce the likelihood of disease transmission among occupants of the particular building space comprises controlling the HVAC system of the building to change the relative humidity in the particular building space relative to a current relative humidity so as to reduce the time a pathogen aerosol will remain in the air.

19. A system for disinfecting a space within a building, the building including a plurality of building spaces, the system comprising:
  a plurality of occupancy sensors distributed throughout each of at least some of the plurality of building spaces of the building;
  a plurality of UV light sources distributed throughout each of at least some of the plurality of building spaces of the building, wherein when activated, the plurality of UV light sources disinfecting at least some surfaces in a corresponding building space;
  a controller operatively coupled to at least some of the occupancy sensors and the plurality of UV light sources, the controller configured to:
    monitor the occupancy sensors to determine when one or more of the plurality of building spaces of the building are unoccupied;
    activating one or more of the plurality of UV light sources in one or more of the plurality of building spaces of the building that are determined to be unoccupied; and
    monitor the occupancy sensors to determine if one or more of the plurality of building spaces of the building where the one or more of the plurality of UV light sources were activated become re-occupied, and if so, deactivating the corresponding UV light sources.

20. The system of claim 19, wherein the controller determines when a building space of the plurality of building spaces is currently indicated as being unoccupied by the occupancy sensors and is expected to remain unoccupied for at least a predetermined period of time based at least in part on a historical occupancy pattern of the building space, and only then determining that the building space is unoccupied.

* * * * *